US007740896B2

(12) United States Patent
Hofer et al.

(10) Patent No.: US 7,740,896 B2
(45) Date of Patent: Jun. 22, 2010

(54) METHOD FOR PRECIPITATING MONO AND MULTIPLE LAYERS OF ORGANOPHOSPHORIC AND ORGANOPHOSPHONIC ACIDS AND THE SALTS THEREOF IN ADDITION TO USE THEREOF

(75) Inventors: Rolf Hofer, Dachsen (CH); Michael Pawlak, Laufenburg (DE); Marcus Textor, Schaffhausen (CH); Eveline Schürmann-Mader, Zeihen (CH); Markus Ehrat, Magden (CH); Samuele Tosatti, Magliaso (CH)

(73) Assignee: Bayer Technology Services GmbH, Leverkusen (DE)

( * ) Notice: Subject to any disclaimer, the term of this patent is extended or adjusted under 35 U.S.C. 154(b) by 0 days.

(21) Appl. No.: 12/230,915

(22) Filed: Sep. 8, 2008

(65) Prior Publication Data

US 2009/0061506 A1     Mar. 5, 2009

Related U.S. Application Data

(62) Division of application No. 10/363,555, filed on Mar. 5, 2003, now Pat. No. 7,517,546.

(51) Int. Cl.
*G01N 1/28* (2006.01)
*G02B 6/00* (2006.01)

(52) U.S. Cl. ......................................... 427/2.11; 365/12
(58) Field of Classification Search ................ 427/2.11; 385/12
See application file for complete search history.

(56) References Cited

U.S. PATENT DOCUMENTS

| 4,005,173 | A |   | 1/1977  | Pemsler et al.  |
|-----------|---|---|---------|-----------------|
| 4,491,531 | A |   | 1/1985  | Bargigia et al. |
| 4,838,556 | A |   | 6/1989  | Sullivan        |
| 5,822,472 | A |   | 10/1998 | Danielzik et al.|
| 5,873,931 | A |   | 2/1999  | Scholz et al.   |
| 5,922,550 | A |   | 7/1999  | Everhart et al. |
| 5,958,430 | A |   | 9/1999  | Campbell et al. |
| 5,959,292 | A |   | 9/1999  | Duveneck et al. |
| 5,997,621 | A |   | 12/1999 | Scholz et al.   |
| 6,078,705 | A |   | 6/2000  | Neuschäfer et al.|
| 6,225,239 | B1|   | 5/2001  | Ohno et al.     |
| 7,517,546 | B2| * | 4/2009  | Hofer et al. ................ 427/2.11 |

FOREIGN PATENT DOCUMENTS

| WO | 96/35940   |    | 11/1996 |
|----|------------|----|---------|
| WO | 97/37211   |    | 10/1997 |
| WO | 98/08077   |    | 2/1998  |
| WO | 98/29580   |    | 7/1998  |
| WO | 98/43086   |    | 10/1998 |
| WO | 99/52574   |    | 10/1999 |
| WO | 99/58963   |    | 11/1999 |
| WO | 00/75644   |    | 12/2000 |
| WO | 01/13096   | A1 | 2/2001  |

OTHER PUBLICATIONS

B. Kasemo et al., "Surface Science Aspects on Inorganic Biomaterials", CRC Critical Reviews in Biocompatibility, vol. 2, Issue 4, pp. 335-380, 1986.
B. Ratner, "New ideas in biomaterials science—a path to engineered biomaterials", Journal Biomedical Materials Research, vol. 27, pp. 837-850, 1993.
J.E. Davies et al., "The migration of osteoblasts over substrata of discrete surface charge", Biomaterials, vol. 7, pp. 231-233, May 1986.

(Continued)

*Primary Examiner*—Raymond J Henley, III
(74) *Attorney, Agent, or Firm*—Wenderoth, Lind & Ponack, L.L.P.

(57) ABSTRACT

The invention relates to a method for precipitating mono or multiple layers of organophosphoric acids of the general formula I (A)

$$Y{-}B{-}OPO_3H_2 \qquad (IA)$$

or of organophosphonic acids of the general formula I (B)

$$Y{-}B{-}PO_3H_2 \qquad (IB)$$

and the salts thereof, wherein B is an alkyl, alkenyl, alkinyl, aryl, aralkyl, hetaryl or hetarylalkyl residue and Y is hydrogen or a functional group from the hydroxy, carboxy, amino, optionally low-alkyl-substituted mono or dialkylamino series, thiol, or a negative acid group from the ester, phosphate, phosphonate, sulfate, sulfonate, maleimide, succinimydyl, epoxy, acrylate series, wherein a biological, biochemical or synthetic indicator element may be coupled to B or Y by addition or substitution reaction, wherein compounds may also be added conferring the substrate surface a resistance to protein adsorption and/or to cell adhesion and in the B chain may optionally be comprised one or more ethylene oxide groups, rather than one or more —CH2— groups. According to the invention, said precipitation occurs on substrate surfaces of pure or mixed oxides, nitrides or carbides of metals and semiconductors, comprising the use of water-soluble salts of a compound of formula (IA) or (IB) for the treatment of these surfaces, in particular as surfaces of sensor platforms, implants and medical accessory devices. The invention also relates to the use thereof as part of coated sensor platforms, implants and medical accessory devices in addition to new organophosphoric acids and organophosphonic acids themselves.

The optionally substituted compounds of formulae (IA) and (IB) wherein the B and Y groups have the above-mentioned designations, i.e. optionally substituted alkyl, alkenyl, alkinyl, aryl, aralkyl, hetaryl or hetaryl, are hereinafter referred to as organophosphoric acids and organophosphonic acids.

29 Claims, 10 Drawing Sheets

OTHER PUBLICATIONS

R. M. Shelton et al., "Interaction Between Primary Bone Cell Cultures and Biomaterials Part 4: Colonization of Charged Polymer Surfaces", Biomaterials and Clinical Applications, pp. 597-602, 1987.

S.-J. Xiao et al., "Covalent Attachment of Cell-Adhesive, (Arg-Gly-Asp)-Containing Peptides to Titanium Surfaces", Langmuir, vol. 14, pp. 5507-5516, 1998.

R.G. Nuzzo et al., "Spontaneously Organized Molecular Assemblies. 3. Preparation and Properties of Solution Adsorbed Monolayers of Organic Disulfides on Gold Surfaces", Journal of the American Chemical Society, vol. 109, pp. 2358-2368, 1987.

John T. Woodard et al., "Self-Assembled Monolayer Growth of Octadecylphosphonic Acid on Mica", Langmuir, vol. 12, pp. 3626-3629, 1996.

D.L. Allara et al., "Spontaneously Organized Molecular Assemblies. 1. Formation, Dynamics, and Physical Properties of n-Alkanoic Acids Adsorbed from Solution on an Oxidized Aluminum Surface", Langmuir, vol. 1, pp. 45-52, 1985.

D.L. Allara et al., "Spontaneously Organized Molecular Assemblies. 2. Quantitative Infrared Spectroscopic Determination of Equilibrium Structures of Solution-Adsorbed n-Alkanoic Acids on an Oxidized Aluminum Surface", Langmuir, vol. 1, pp. 52-66, 1985.

Iris Maege et al., "Ultrathin Organic Layers for Corrosion Protection", Macromol. Symp., vol. 126, pp. 7-24, 1997.

Marcus Textor et al., "Structural Chemistry of Self-Assembled Monolayers of Octadecylphosphoric Acid on Tantalum Oxide Surfaces", Langmuir, vol. 16, pp. 3257-3271, 2000.

Dorothee Brovelli et al., "Highly Oriented, Self-Assembled Alkanephosphate Monolayers on Tantalum (V) Oxide Surfaces", Langmuir, vol. 15, pp. 4324-4327, 1999.

Waichiro Tagaki et al., "The Syntheses and Hydrolyses of p-Substituted Phenyl Phosphosulfates", Bulletin of the Chemical Society of Japan, vol. 44, pp. 1139-1141, 1971.

Toshio Eiki et al., "Phosphonosulfates. Metal Ion Catalysis in the Hydrolysis of 2-Pyridyl- and 2-Pyridylmethylphosphonosulfate", J. Am. Chem. Soc., vol. 104, pp. 1986-1991, 1982.

Kenneth C. Ross et al., "Use of Bis[2-(trialkylsily)ethyl] N,N-Dialkylphosphoramidites for the Synthesis of Phosphate Monoesters", J. Chem. Soc., Perkin Trans. 1, vol. 4, pp. 421-426, 1995.

International Search Report dated Aug. 28, 2002 in the International Application PCT/EP01/10077 corresponding to parent application of present divisional application.

* cited by examiner

METHOD FOR PRECIPITATING MONO AND MULTIPLE LAYERS OF ORGANOPHOSPHORIC AND ORGANOPHOSPHONIC ACIDS AND THE SALTS THEREOF IN ADDITION TO USE THEREOF

This application is a divisional application of Ser. No. 10/363,555, filed Mar. 5, 2003, now U.S. Pat. No. 7,517,546, which is 371 application of PCT/EP01/10077, filed Aug. 31, 2001.

The invention relates to a method for precipitating mono or multiple layers of organophosphoric acids with the general formula I (A)

$$Y-B-OPO_3H_2 \quad (IA)$$

or of organophosphonic acids with the general formula I (B)

$$Y-B-PO_3H_2 \quad (IB)$$

and the salts thereof, wherein B is an alkyl, alkenyl, alkinyl, aryl, aralkyl, hetaryl or hetarylalkyl residue and Y is hydrogen or a functional group from the hydroxy, carboxy, amino, optionally low-alkyl-substituted mono or dialkylamino series, thiol, or a negative acid group from the ester, phosphate, phosphonate, sulfate, sulfonate, maleimide, succinimydyl, epoxy, acrylate series, wherein a biological, biochemical or synthetic recognition element may be coupled to B or Y by addition or substitution reaction, wherein compounds may also be added conferring the substrate surface a resistance to protein adsorption and/or to cell adhesion and in the B chain may optionally be comprised one or more ethylene oxide groups, rather than one or more $-CH_2-$ groups. According to the invention, said precipitation occurs on substrate surfaces of pure or mixed oxides, nitrides or carbides of metals and semiconductors, comprising the use of water-soluble salts of a compound of formula (IA) or (IB) for the treatment of these surfaces, in particular as surfaces of sensor platforms, implants and medical accessory devices. The invention also relates to the use thereof as part of coated sensor platforms, implants and medical accessory devices in addition to new organophosphoric acids and organophosphonic acids therein.

The optionally substituted compounds of formulae (IA) and (IB) wherein the B and Y groups have the above-mentioned designations, i.e. optionally substituted alkyl, alkenyl, alkinyl, aryl, aralkyl, hetaryl or hetaryl, are hereinafter referred to as organophosphoric acids and organophosphonic acids.

For the preparation of sensor surfaces with biological or biochemical recognition elements immobilized on a so-called transducer for highly efficient and highly selective binding of one or more analytes to be detected in a sample, the nature of the transducer surface is of great importance. To achieve the lowest possible limits of detection, it is desirable to immobilize in a small space as many recognition elements as possible to which as many analyte molecules of one variety as possible may then be bound in the later detection process. At the same time it is desirable on immobilization to obtain as high a degree of reactivity and biological or biochemical functionality of the recognition elements as possible, i.e. to minimize any signs of denaturation resulting from the immobilization. A further objective is as far as possible to prevent the non-specific binding or adsorption of analyte molecules which in many cases have the effect of restricting the limits of detection attainable. To fulfill these functions, a number of different methods of chemical modification have been developed with the aim of manufacturing so-called biocompatible surfaces. To some extent similar demands are made in medicine with regard to the nature of implant surfaces.

In the field of medical implants, such as dental implants, artificial hip joints or intravascular stents, or of biomedical devices, such as catheters or endoscopes, the nature of the surface has a significant effect on the functionality of the part (B. Kasemo, J. Lausmaa, "Surface Science Aspects on Inorganic Biomaterials", *CRC Crit. Rev. Biocomp.* 2 (1986), 335-380). The main reason for this is the fact that, after implantation in the body, the surface of the implant forms the boundary between the biological environment and the foreign material, where important processes take place, such as foreign-body reactions, inflammations, cell adhesion and formation of new tissue. Of particular importance is the adsorption of proteins from body fluids (blood, intercellular fluid etc.), since these processes take place soon after the implantation and regulate the further biologically important processes, in particular the accumulation of cells. The surface properties of the implant are crucial here, because they directly determine the nature of the proteins, their strength of binding to the surface and their conformation and orientation (B. Ratner, "New ideas in biomaterials science—a path to engineered biomaterials", *J. Biomed. Mat. Res.* 27 (1993), 837-850). These remarks are applicable to a wide variety of applications. Examples in the field of metallic implants are:

1. Permanently or temporarily implanted components of steel, cobalt-chromium alloys, titanium or titanium alloys in the skeletal area, such as artificial hip joints, dental root implants, osteosynthesis plates or screws. The desired objective here is to achieve adsorption of cell-adhesive proteins which favorably influence the integration of the part into the bone (osteointegration).
2. Metallic parts of steel, titanium or nickel-titanium alloys which assume functions in contact with blood, such as stents in blood vessels, to provide permanent prevention of arterial or venous closure. Such parts must show a compatibility with blood which meets the specific requirements. Often an implant surface is required here which is resistant to protein adsorption and to platelet adhesion and is thus a surface which shows only minimal if any tendency towards undesirable thrombosis formation.
3. Parts of titanium or steel which are in contact with soft tissue, e.g. in osteosynthesis applications to support the healing of bone fractures or in dental implants that come into contact with gingival tissue. It is often the aim here that the soft tissue should lie very close to the implant, but not form a firm connection therewith.

If the surfaces of such implants can be specifically adjusted to the conditions of use, the above-mentioned processes can be favorably influenced and the functionality of the implant thus decisively improved. There is a whole range of surface properties which have been proven or hypothetically deduced to influence compatibility with the specific application in the body:

1. The wettability of the surface or repulsion of water by the surface (hydrophilicity/hydrophobicity of the surface, measured e.g. as contact angle with water), which is associated with surface energy. In this respect, it may be of advantage to set an ideal wettability with water for a particular application.
2. The charge of the surface (positive, negative or no charge) shows a marked influence on the behavior of cells at the surface of an implant, for example on that of bone cells (J. E. Davies, B. Causton, Y. Bovell, K. Davy, C. S. Sturt, "The Migration of Osteoblasts Over Substrata of Discrete Surface-Charge", *Biomaterials*, Vol. 7 (1986), 231-233; R. M.

Shelton, I. M. Whyte, J. E. Davies, "Interaction between Primary Bone Cell and Biomaterials. Part 4: Colonization of Charged Polymer Surfaces"; *Biomaterials and clinical applications: proceedings of the Sixth European Conference on Biomaterials*, Bologna, Italy, Sep. 14-17, 1986; Elsevier; 1987; 597-602).

3. The presence of functional groups or biological molecules which are applied to the surface of the implant and, following implantation, influence the biological process on the surface. Said molecules include e.g. specific peptides, proteins or growth factors (S.-J. Xiao, M. Textor, N. D. Spencer, H. Sigrist, "Covalent Attachment of Cell-Adhesive, RGD-Containing Peptides on Titanium Surfaces", *Langmuir* 14 (1998), 5508-16, 1998).
4. The presence of protein-repellent molecules, such as polyethylene oxide, polyethylene glycol or heparin on the surface.

The chemical properties of the surface of commercial implants are often not optimized for the application to an extent that one might wish for the medical application. The chemical properties are also often only incompletely controlled in commercial production. Impurities are observed which are the consequence of processing or storage conditions. Such impurities are potentially harmful for application in the body. In addition they are usually not consistent from one production batch to another or throughout the storage period and pose a risk with respect to the quality assurance of medicinal products. Particular susceptibility to such impurities is shown by metallic implants such as those made of steel or other iron alloys, or titanium and alloys thereof (TiAlV, TiAlNb, etc.), or cobalt-chromium alloys (CoCr, CoCrMo), all of which are coated with a thin, natural oxide layer of high surface energy and thereby especially prone to contamination from the environment (e.g. through adsorption of organic components from the air, such as hydrocarbons, alcohols, etc., or through adsorption from liquids (adsorption of silicone oils, etc.).

The object of the invention is the provision of such a method for the treatment of surfaces, especially of oxides, nitrides or carbides of metals or semiconductors or mixtures thereof or of oxide-coated metals or semiconductors, using monolayers or multiple layers of organophosphoric or organophosphonic acids or derivatives thereof as defined hereinabove, in particular the salts thereof, in order to produce surfaces which show a reproducible chemical composition and to adapt the properties of these surfaces for the specific application in the field of biomaterials/implants and biosensors.

Coating compounds and methods for the antireflection and antimist coating of surfaces are described in U.S. Pat. Nos. 5,997,621 and 5,873,931. The use of a range of different amphipaths is named, but their combination with porous metal oxides, which are present for example in a dispersion, only serves the formation of a network of metal oxides and amphipaths which are then applied in turn to the surface to be coated. There are no references to a coating with amphipaths in a process of self-organization (formation of "self assembled monolayer").

The application of self-assembled monolayers to metal-coated plastic films by means of a stamping process is described in U.S. Pat. No. 5,922,550, wherein analyte-specific receptors are inserted into the monolayers to be applied. Solid substrates or other materials as carriers for the metal coating (of gold, silver, aluminum, chrome, copper, zirconium, platinum and nickel, as well as oxides thereof) are not described.

Not mentioned in particular is a precipitation process of the self-assembled monolayer (SAM) on a metal oxide film which would be suitable as an optical waveguide as described in a preferred embodiment of our method according to the invention. Although alkyl phosphonates or phosphonic acids are mentioned, no alkyl phosphates or alkyl phosphoric acids are mentioned.

The use of dodecylphosphate ammonium salt ($DDPO_4$ ammonium salt, $DDPO_4(NH_4)_2$ is described in a number of patents (for example U.S. Pat. Nos. 4,005,173; 4,491,531; 4,838,556; 5,873,931; 5,997,621), but not the use thereof for the formation of a self-assembled monolayer on a macroscopic substrate through precipitation from aqueous solution.

In J. G. van Alsten, "Self-assembled monolayers on engineering metals: structure, derivatization and utility", *Langmuir* 15 (1999) 7605-7614, the precipitation of SAMs based on alkyl phosphonic acids from aqueous and alcoholic solutions on so-called engineering metals (steel, aluminum, copper, and brass) is described, but not the formation of SAMs based on alkyl phosphoric acids or derivatives thereof.

In WO 98/29580, a method is described for the treatment of metallic surfaces of zinc, magnesium, aluminum or alloys thereof by spraying, immersion or roller-coating to improve the adhesion and corrosion resistance of lacquered and plastic-coated products. This method describes alkyl phosphoric acids or alkyl phosphonic acids and derivatives thereof with 2-50 carbon atoms in the alkyl chain and various terminal functional groups. The precipitation occurs from aqueous solution, wherein the solubility of some of these compounds is enhanced by the addition of organic solvents. The poorly water-soluble phosphonic acids with a terminal methyl group, such as 1-phosphonic acid dodecane or 1-phosphoric acid octadecane, have not been described. By contrast, hydroxy-terminated molecules, such as 1-phosphoric acid-12-hydroxydodecane, have been described. The use of this class of molecule is confined to the above-mentioned metals, and after surface treatment a further compact organic coat, e.g. a lacquer or plastic, is applied. The metal layer modified for example with alkyl phosphoric or alkyl phosphonic acids or derivatives thereof thus never serves as an outer coating exposed to the environment.

For some years, surfaces have been modified using so-called self-assembled monolayers (hereinafter abbreviated as "SAMs"). These are very thin, monomolecular layers which form spontaneously through the contact of a surface with a solution of the corresponding molecule and are characterized by an organized structure of the molecule chain. The best-known are long-chain alkylthiols, which form SAMs of gold surfaces (R. G. Nuzzo, F. A. Fusco, D. L. Allara, "Spontaneously Organized Molecular Assemblies 0.3. Preparation and Properties of Solution Adsorbed Monolayers of Organic Disulfides On Gold Surfaces"; *Journal of the American Chemical Society*, 109 (1987), 2358-2368)). Although such gold/alkylthiol SAM surfaces are used in the biomedical field as model surfaces thanks to their perfectly controlled chemical surface properties, they are of no interest for the manufacture of implants, because gold is only of minor importance in this field of application.

However, gold surfaces play a greater role in the field of bioanalytics. The phenomenon of surface plasmon resonance, for example, is characteristic of a certain type of thin metal films, in particular of gold. In recent years, therefore, surface modification by means of SAM production from alkylthiols has especially been used in this field.

On the other hand, it has been shown that alkyl phosphates adsorb to oxidic surfaces. This was demonstrated for the first time on mica surfaces (J. T. Woodward et al., *Langmuir* 12

(1996) 6429) and on aluminum surfaces (D. L. Allara, R. G. Nuzzo, "Spontaneously Organized Molecular Assemblies 0.1. Formation, Dynamics, and Physical-Properties of Normal-Alkanoic Acids Adsorbed From Solution On an Oxidized Aluminum Surface", *Langmuir* 1 (1985), 45-52; D. L. Allara, R. G. Nuzzo, "Spontaneously Organized Molecular Assemblies 0.2. Quantitative Infrared Spectroscopic Determination of Equilibrium Structures of Solution-Adsorbed Normal-Alkanoic Acids On an Oxidized Aluminum Surface", *Langmuir* 1 (1985), 52-66; I. Maege, E. Jaehne, A. Henke, H.-P. Adler, C. Bram, C. Jung, M. Stratmen, *Macromol. Symp.* 126 (1997), 7-24). The monolayers formed on mica, however, were not very stable and thus of minimal relevance for technical applications. By contrast, it was found that octadecylphosphate on tantalum oxide ($Ta_2O_5$) forms SAMs which are structurally very similar to those of thiols on gold and also considerably more stable than on mica (M. Textor, L. Ruiz, R. Hofer, A. Rossi, K. Feldman, G. Hähner, N. D. Spencer, "Structural Chemistry of Self-Assembled Monolayers of Octadecylphosphoric Acid on Tantalum Oxide Surfaces" *Langmuir* 16 (2000), 3257-3271; D. Brovelli, G. Hähner, L. Ruiz, R. Hofer, G. Kraus, A. Waldner, J. Schlösser, P. Oroszlan, M. Ehrat, N. D. Spencer, "Highly Oriented, Self-Assembled Alkanephosphate Monolayers on Tantalum(V) Oxide Surfaces", *Langmuir* 15 (1999), 4324-4327). The technology of self-assembled layers of octadecylphosphate allows the surface of tantalum oxide to be rendered extremely hydrophobic thanks to the organized structure of the hydrophobic alkyl chains (contact angle with water: 112-115°) (FIGS. 1 and 2).

Since alkyl phosphates in which B and Y have the aforementioned designations, for example, can in principle also be furnished with terminal groups other than methyl, e.g. with hydroxyl (—OH), amine (—$NH_2$) or carboxyl (—COOH), the technology naturally offers the opportunity to apply specific chemical treatments to oxide-coated medical implant surfaces or (optical) sensors with an oxide surface and to adapt the chemical surface properties to the application in question and preserve its stability.

These organized alkyl phosphate layers on tantalum oxide were produced through contact of the oxidic surfaces with a solution of the alkyl phosphate on the basis of organic solvents (heptane/isopropanol). Aqueous solutions could therefore not be used, because these long-chain alkyl phosphates are not sufficiently water-soluble.

Although short-chain alkyl phosphates would be sufficiently water-soluble, they form almost no SAMs, because the interactions between the long alkyl chains within the organized layer of the adsorbate are necessary for the formation of oriented chains and organization.

If the surface treatment process has to be carried out in organic solvents, problems arise which at least substantially restrict, if not hinder altogether, any commercial applications:

1. This type of modification is limited to the surfaces of substrates whose materials show a sufficiently high degree of resistance to organic solvents. For example, such a process of surface modification for metal or metal oxide films on plastic substrates can be virtually excluded.
2. The use of volatile organic solvents is associated with emissions which pose a burden on the workplace, the environment and the atmosphere. Legislation in many countries has become very strict in this respect and in various industries has led to such solvents being completely supplanted by processes which cause few if any environmental problems.
3. If these emissions are to be eliminated, a substantial increase in costs can be expected (closed systems, purification of exhaust air, recovery of solvents). The resulting increase in costs often has such a negative impact on the economic balance that such processes become unattractive for commercial production.
4. Specifically in the case of biomaterials and implants, organic solvents have the serious disadvantage that they often have a cytotoxic effect or exert a negative influence on the development of cells and tissues. Since SAMs produced from organic solvents are never entirely free of organic solvents, there is always a risk that the organic volatile molecules remaining in the SAM may have a subsequent negative effect in the body.
5. It often has to be anticipated that the desired specific properties cannot be achieved by a single type of molecule, but requires a composite of SAM molecules. However, since different SAMs have very different solubility in organic solvents (especially in case of ω-terminal groups of differing polarity), it is often difficult if not impossible to find a single solvent which permits the production of a mixture of two (or more) molecules for the precipitation of a composite SAM.

According to this invention, the aim is to eliminate the above-mentioned disadvantages in the manufacture of SAMs, based on the organophosphates or organophosphonates defined hereinbefore or derivatives thereof, in particular salts, functionalized organophosphates or corresponding phosphonates, and to develop a method which allows the formation of well-defined SAMs on a number of metal, semiconductor, oxide, carbide or nitride surfaces without the use of solvents and the production of layers which comprise two or more different, functionalized and/or nonfunctionalized organophosphates or -phosphonates.

The invention relates to a method for precipitating mono or multiple layers of organophosphoric acids with the general formula I (A)

Y—B—$OPO_3H_2$ (IA)

or of organophosphonic acids with the general formula I (B)

Y—B—$PO_3H_2$ (IB)

and the salts thereof, on substrate surfaces of pure or mixed oxides, nitrides or carbides of metals and semiconductors, wherein B is an alkyl, alkenyl, alkinyl, aryl, aralkyl, hetaryl or hetarylalkyl residue and Y is hydrogen or a functional group from the hydroxy, carboxy, amino, optionally low-alkyl-substituted mono or dialkylamino series, thiol, or a negative acid group from the ester, phosphate, phosphonate, sulfate, sulfonate, maleimide, succinimydyl, epoxy, acrylate series, wherein a biological, biochemical or synthetic recognition element may be coupled to B or Y by addition or substitution reaction, wherein compounds may also be added conferring on the substrate surface a resistance to protein adsorption and/or to cell adhesion and in the B chain may optionally be comprised one or more ethylene oxide groups, rather than one or more —CH2— groups, characterized in that water-soluble salts of a compound of formula (IA) or (IB) are used for the treatment of these surfaces, in particular as surfaces of sensor platforms, implants and medical accessory devices. The invention also relates to the use thereof as part of coated sensor platforms, implants and medical accessory devices in addition to new organophosphoric acids and organophosphonic acids themselves.

The invention especially relates to methods for precipitating mono or multiple layers of organophosphoric acids of formula I (A) or of organophosphonic acids of formula I (B)

and salts thereof, wherein groups B and Y are combined to form an alkyl group or an optionally substituted alkyl group of 2-24 C atoms.

The invention relates in particular to methods for precipitating mono or multiple layers of organophosphoric acids of formula I (A) or of organophosphonic acids of formula I (B) and salts thereof, wherein groups B and Y are combined to form an alkyl group or an optionally substituted alkyl group of 2-12 C atoms.

Most particularly, depending on the intended scope of use, the invention relates also to methods for precipitating mono or multiple layers of organophosphoric acids of formula I (A) or of organophosphonic acids of formula I (B) and salts thereof, wherein groups B and Y are combined to form an alkyl group or an optionally substituted alkyl group of 2-5 C atoms.

Suitable substituents are especially the substituents listed in the introduction under Y.

The preferred layers, i.e. mono and multiple layers of organophosphoric acids of formula I (A) and organophosphonic acids of formula I (B) are also suitable for use as part of coated sensor platforms, implants and medical accessory devices.

Preferably compounds of formula I (A) or I (B) with various chain lengths are used, depending on the intended scope of use.

Alkyl is for example C2-C24alkyl, such as ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosanyl, heneicosanyl, docosanyl, tricosanyl or tetracosanyl. Alkenyl is for example ethylene, propylene, butylene, pentylene, 2-methylpentene-(1) and other higher-member alkenyls such as hexadecenyl, heptadecenyl or also octadecenyl.

Alkinyl is for example ethinyl, 2-propinyl, 2- or 3-butinyl or also higher-member alkinyls such as 4-pentinyl.

Aryl as such is e.g. phenyl or naphthyl, such as e.g. 1- or 2-naphthyl or substituted phenyl or naphthyl, such as phenyl or naphthyl which apart from Y are additionally substituted by lower alkyl, halogen-lower alkyl, hydroxy, lower alkoxy, lower alkanoyloxy, halogen, and/or cyano. Aryl is preferably unsubstituted phenyl or phenyl substituted as indicated above, in particular phenyl.

Arylalkyl is preferably aryl-lower alkyl, in particular phenyl-lower alkyl, quite especially phenylethyl or benzyl.

Lower alkoxy is e.g. n-propoxy, isopropoxy, n-butoxy or tert-butoxy, preferably ethoxy and in particular methoxy.

Lower alkanoyloxy is for example propionyloxy or pivaloyloxy, preferably acetyloxy.

Halogen is for example chlorine or fluorine, in the broader sense also bromine and iodine.

Halogen-lower alkyl is for example 2- or 3-halogen-lower alkyl, for example 2-halopropyl, 3-halopropyl or 3-halo-2-methylpropyl.

Hetaryl is understood to mean especially a monocyclic, but also a bicyclic or polycyclic residue of an aromatic character. Bicyclic and polycyclic hetaryl may be composed of several heterocyclic rings or preferably of one heterocyclic and one or more, e.g. one or two and in particular one, annellated carbocyclic ring, in particular a benzo ring. Each individual ring comprises e.g. 3, 5, 6, 7 and in particular 5 or 6 ring members.

Hetaryl is in particular an aza, thia oxa, thiaza, oxaza, diaza and tetrazacyclic residue.

Hetaryl is especially a monocyclic monoaza, monothia or monooxacyclic residue, such as pyrryl, e.g. 2-pyrryl or 3-pyrryl, pyridyl, thienyl, e.g. 2- or 3-thienyl, or furyl, e.g. 2-furyl, bicyclic monoaza, monooxa or monothiacyclic residue, e.g. indolyl, e.g. 2- or 3-indolyl, quinolinyl, e.g 2- or 4 quinolinyl, isoquinolyl, 1-isoquinoline, benzofuran, e.g. 2- or 3-benzofuranyl, or benzothienyl, e.g. 2- or 3-benzothienyl, monocyclic diaza, triaza, tetraza, oxaza, thiaza or thiadiazacyclic residue, such as imidazolyl, e.g. 2-imidazolyl, pyrimidinyl, e.g. 2- or 4-pyrimidinyl, triazolyl, e.g. 1,2,4-triazol-3-yl, tetrazolyl, e.g. 1- or 5-tetrazolyl, oxazolyl, e.g. 2-oxazolyl, isoxazolyl, e.g. 3- or 4-isoxazolyl, thiazolyl, e.g. 2-thiazolyl, isothiazolyl, e.g. 3- or 4-isothiazolyl or 1,2,4- or 1,3,4-thiadiazolyl, e.g. 1,2,4-thiadiazol-3-yl or 1,3,4-thiadiazol-2-yl, or bicyclic diaza, oxaza, thiazacyclic residue, such as benzimidazolyl, e.g. 2-benzimidazolyl, benzoxazolyl, e.g. 2-benzoxazolyl or benzthiazoyl, e.g. 2-benzthiazolyl.

Hetaryl residues are unsubstituted or carry substituents as indicated under aryl.

Hetaryl is especially pyridyl, thienyl, pyridyl or furyl.

Hetarylalkyl residues are composed of the above-mentioned hetaryl residues and the previously named alkyl residues.

The organophosphoric acids of formula I (A) and organophosphonic acids of formula (IB) used in the method according to the invention may form salts with bases, e.g. corresponding alkali metal or alkaline earth metal salts, e.g. sodium, potassium or magnesium salts, and in the broader sense also transition metal salts, such as zinc and copper salts, or in particular salts with ammonia or organic amines, such as cyclic amines, such as mono-, di- or tri-lower alkylamines, such as hydroxy-lower alkylamines or polyhydroxy-lower alkylamines. Cyclic amines are e.g. morpholine, thiomorpholine, piperidine or pyrrolidine. Suitable mono-lower alkylamines are for example ethyl and tert-butylamine, suitable di-lower alkylamines are for example diethyl and diisopropylamine, and suitable tri-lower alkylamines are for example trimethyl and triethylamine, which form quaternary ammonium salts.

Appropriate hydroxy-lower alkylamines are e.g. mono-, di- and tri-ethanolamine, hydroxy-lower alkylamines are e.g. N,N-dimethyl-amino- and N,N-diethylamino ethanol. Included in the broader sense are also the above-mentioned transition salts, which may be unsuitable for use, but may be of advantage for the isolation or purification of organophosphoric acids of formula I (A) or organophosphonic acids of formula I (B).

As carboxyl group, substituent Y may also form analogous basic salts.

As substituents, organophosphoric acids of general formula I (A) and organophosphonic acids of general formula I (B) may also show a basic Y group.

For example, when Y is amino or optionally amino substituted by lower alkyl or di-lower alkyl. Compounds with a basic Y group may be e.g. acid addition salts with suitable mineral acids, such as hydrogen halides, sulfuric acid or phosphoric acid, e.g. hydrochlorides, hydrobromides, sulfates, hydrogen sulfates or phosphates, salts with suitable aliphatic or aromatic sulfonic acids or N-substituted sulfamic acids, e.g. methanesulfonates, benzenesulfonates, p-toluenesulfonates or N-cyclohexylsulfaminates (cyclamates), or salts with strong organic carboxylic acids, such as lower alkanecarboxylic acids.

Also an object of the invention are new organophoshoric acids of the formula

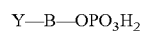 (IA)

and organophosphonic acids of formula

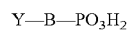 (IB)

wherein B and Y have the designations indicated hereinabove with the exception of the shared designation of alkyl and salts thereof.

In particular the invention relates to new organophosphoric acids of formula I (A) and organophosphonic acids of formula I (B) wherein B and Y are an aryl or arylalkyl residue and salts thereof.

The invention comprises the production of a salt of the free organophosphoric acid or organophosphonic acid in water, in a different solvent or a mixture and the simultaneous or subsequent precipitation of the corresponding salt by the introduction of a base which forms the cation in the resulting salt. The precipitation takes place either spontaneously or after a corresponding cooling or concentration of the solution. Suitable cations are all customary positively charged particles, such as alkali metals (e.g. $Na^+$, $K^+$), the alkaline earth metals, ammonium ($NH_4^+$) or other quaternary ammonium ions (e.g. tetrabutylammonium). The formation of salt here takes place through introduction of the appropriate aqueous base (e.g. KOH or $NH_4OH$) into the solution of the organophosphoric or organophosphonic acid, or through the introduction of a base in an organic solvent (e.g. tetrabutylammonium hydroxide in alcoholic solution) into the solution of the organophosphoric or organophosphonic acid, or through the introduction of a base that is volatile (gaseous) at room temperature or at elevated temperatures (such as ammonia or a volatile amine) into the solution of the organophosphoric or organophosphonic acid. The resulting, saline compound then has either an inadequate solubility in the selected solution and precipitates out spontaneously as a salt, or the precipitation is attained by cooling or concentration of the solvent volume. It is preferred that sodium, potassium or ammonium salts in particular be used as salts of compounds of formula (IA) and/or (IB). Especially preferred here is formation of the ammonium salt because, thanks to its low affinity for surfaces, ammonium does not interfere at all in the formation of the SAM in the subsequent SAM process.

A further advantage of these salts for their use in the method according to the invention is the fact that they can then be readily purified by recrystallization and freed from unwanted impurities of the free acid.

An important characteristic of the method according to the invention is thus that the water-soluble salt of a compound of formula (IA) and/or (IB) is isolated before the precipitation of said mono or multiple layers.

Although preparation of the ammonium salt of dodecanephosphoric acid has already been described (see above), it has not been described for use as a salt in a subsequent SAM process based on an aqueous solution of the corresponding salt.

Use of the resulting salts according to the invention relates to the use of aqueous solutions of the salt in the SAM formation process for the treatment of oxide, carbide or nitride surfaces as specified above. As a result, not only is it possible to produce SAMs which are free of unwanted solvent impurities, but it is also very easy to prepare aqueous mixtures of several salts of different functionalized and/or nonfunctionalized organophosphates and/or organophosphonates.

A further important and advantageous characteristic of the method according to the invention is thus that the said mono or multiple layers of compounds of formula (IA) and/or (IB) are free of organic solvents.

The preparation of SAMs from aqueous solution of (soluble) organophosphate or organophosphonate derivatives and the formation of sodium and potassium salts of organophosphates or organophosphonates directly in aqueous solution is likewise described in WO 98/29580 (see above). The differences from the present invention are as follows:

1. According to the description in WO 98/29580, the salts are not isolated, but are simply prepared in situ. As a result, the preferred purification option through recrystallization of the salt before it is used for the formation of SAMs is not applicable. In addition, this method allows a highly controlled adjustment of the stoichiometry of the SAM solution to be used.
2. The applications relate to completely different application fields with completely different requirements (lacquer adhesion, corrosion protection for lacquered products) on different substrate materials (of zinc, aluminum, magnesium or alloys thereof).

Suitable substrates for the application of surface treatment methods according to the invention are the following materials: Oxides, nitrides or carbides of tantalum, niobium, titanium, vanadium, zirconium, hafnium, molybdenum, tungsten, silicon or mixtures thereof in the form of solid bodies or as layers on substrates of any kind. Particularly suitable are metals or metal alloys which show an oxide layer on the surface that results either from a natural, spontaneous formation or from artificial production (e.g. by anodization), these being preferably the metals titanium, tantalum, niobium, vanadium, zirconium, hafnium, molybdenum, tungsten, or silicon or alloys of these metals or semiconductors.

Of major importance here are optically transparent oxides for applications in the field of optical biosensors, e.g. for sensors based on the principle of optical waveguide technology. These include in particular, but not exclusively, metal oxides with a high refractive index, such as tantalum oxide ($Ta_2O_5$), niobium oxide ($Nb_2O_5$), titanium oxide ($TiO_2$), zirconium oxide ($ZrO_2$) and mixtures of these oxides.

Particularly worthy of mention in the field of biomaterials are oxide-ceramic materials, such as aluminum oxide ($Al_2O_3$) and zirconium oxide ($ZrO_2$). Since metallic materials with biocompatible properties almost always form a natural oxide layer on the surface (passive layer, responsible for corrosion resistance and biocompatibility), the method according to the invention can be advantageously applied also to a number of implant materials. The materials to be mentioned in this field are titanium (with $TiO_2$ surface), niobium (with $Nb_2O_5$ surface), zirconium (with $ZrO_2$ surface) and tantalum (with $Ta_2O_5$ surface). Furthermore, the method can be applied to alloys, in particular to Ti—Al—V, Ti—Al—Nb, Ti—Nb—Zr, Ti—Nb—Zr—Ta, chrome-nickel-steel (Fe—Cr—Ni, Fe—Ni—Mo), Co—Cr and Co—Cr—Mo.

Whereas essentially smooth, planar substrates are often used in sensors (but not always—capillary-based sensors are an example), the surfaces which are of interest in biomaterials or the implant field are often rough surfaces or surfaces with a topographically specific structure, because in certain applications they induce a preferred biological reaction in the body. Especially in metallic implants for the skeletal area (artificial hip joints, dental implants, osteosynthesis plates and screws) often rough or specifically roughened surfaces are used (Sittig 98). Such surfaces with complex surface topography or porosity frequently pose particular problems where the setting of specific chemical properties is concerned. The method according to the invention for forming SAMs based on alkyl phosphates, alkylphosphonates and the functionalized derivatives thereof (see also below) opens up particularly interesting opportunities for functionalizing such complex, rough metal surfaces, because the method is equally applicable on rough, structured or porous surfaces of oxide-coated metals and metal oxides. This is explained in detail in Example 2.

The method of surface modification according to the invention is thus suitable for substrates which show an almost smooth surface with little roughness and also for substrates which have rough surfaces, whereby these surfaces may show an additional structuring.

It is especially preferred for biosensor applications that materials for biochemical, biological or synthetic recognition elements (coupled to B or Y) be selected from among the group of nucleic acids, such as DNA, RNA, oligonucleotides, nucleic acid analogs, such as PNA, monoclonal or polyclonal antibodies, peptides, enzymes, aptamers, synthetic peptide structures, soluble membrane-bound proteins and proteins isolated from a membrane, such as receptors, ligands thereof, antigens for antibodies, biotin, "histidine tag components" and complexing partners thereof.

It is especially preferred, however, for applications of the method according to the invention for biologically compatible surface modification of implants that a biologically effective recognition element comprises peptides, proteins, glycoproteins, growth factor, such as TGF-β, or BMP (bone morphogenic protein).

Using the method according to the invention, it is also possible to produce strongly hydrophobic surfaces which can be passivated for example by contact with albumins (for example, human serum albumin (HSA) or bovine serum albumin (BSA)) to achieve a protein-resistant surface. This may be important for applications for example in the field of devices which come into contact with blood (blood compatibility, prevention of platelet adsorption and thrombus formation).

For this purpose it may be advantageous to add to B or Y a compound which confers on the substrate surface a resistance to protein adsorption and/or cell adhesion, wherein this compound is preferably selected from the group of compounds which are formed from oligo(ethylene oxide), phosphoryl choline, heparin, saccharides, albumins, especially bovine serum albumin or human serum albumin, casein, nonspecific, polyclonal or monoclonal, heterologous or for the analyte or analytes to be determined empirically nonspecific antibodies (especially for immunoassays), detergents (such as Tween 20), fragmented natural DNA or synthetic DNA not hybridizing with polynucleotides for analysis, such as a herring or salmon sperm extract (especially for polynucleotide hybridization assays), or also uncharged, but hydrophilic polymers, such as polyethylene glycols or dextrans. Groups such as oligo(ethylene oxide) show particularly good behavior in respect of protein resistance and have already been described with other systems, e.g. with thiol-based SAMs on gold surfaces (P. Harder, M. Grunze, R. Dahint, G. M. Whitesides, P. E. Laibinis, J. Phys. Chem. B, 102 (1998), 426-436). Typical applications serve for example to improve the blood compatibility of stents or to prevent platelet adsorption and thrombus formation in contact with circulating blood.

It is also possible that compounds of formula (IA) and/or (IB) comprise various functional groups and/or biological or biochemical or synthetic recognition elements and/or compounds for conferring on the surface a resistance to protein adsorption and/or cell adhesion in the same SAM molecule, e.g. a protein-resistant oligo(ethylene oxide) group in combination with a biological recognition element, such as biotin.

Within the terms of the invention, it is also possible that a secondary or further sequential monolayer might be precipitated on a primary monolayer of organophosphates and/or organophosphonates, so that a double or multiple layer is produced on said substrate surfaces.

A possible variant of the method comprises producing from the primary monolayer of organophosphates and/or organophosphonates a hydrophobic surface on which a further layer of synthetic or natural lipids is precipitated.

In a special embodiment, the method comprises producing the said additional layer of synthetic or natural lipids from a lipid vesicle suspension through spontaneous attachment of the vesicles to the hydrophobic surface of a primary monolayer of organophosphates and/or organophosphonates, followed by distribution of the vesicle membrane on this primary monolayer.

The synthetic or natural lipids may be selected from a group which is formed from phosphoglycerol lipids etc. or which comprises a mixture of these molecules. According to the embodiment described hereinbefore, molecular groups Y and/or B and/or biological or biochemical or synthetic recognition elements and/or compounds which confer on the surface a resistance to protein adsorption and/or cell adhesion may be associated with the said additional layer.

A preferred embodiment of the method according to the invention comprises immobilizing synthetic or natural vesicles or microsomes on a multiple layer with a first monolayer of organophosphates and/or organophosphonates on a substrate surface, optionally with associated biological or biochemical or synthetic recognition elements selected from a group which is formed from nucleic acids (for example DNA, RNA, oligonucleotides) and nucleic acid analogs (e.g. PNA), monoclonal or polyclonal antibodies, peptides, enzymes, aptamers, synthetic peptide structures, soluble, membrane-bound proteins and proteins isolated from a membrane, such as receptors, ligands thereof, antigens for antibodies, biotin, "histidine tag components" and complex-forming partners thereof.

A further embodiment is the use of mixtures of various SAM molecule. Such mixed SAM layers may be produced in two ways: either by preparation of an aqueous solution which contains both SAM types, followed by treatment of the surface in this mixture, or by sequential adsorption using pure SAM solutions in each case. An example of using different SAM molecules in aqueous solution to form mixed SAM systems on the surface is precipitation from a mixture of SAM molecules which comprise a biological recognition element such as biotin and SAM molecules which comprise a group such as oligo(ethyleneoxide) to produce a surface with a protein-resistant background in the simultaneous presence of a biologically specific function (biotin).

SAMs are described as mixed when they comprise two molecules in any ratio, wherein the above-mentioned classes of molecules may be represented in any combination.

A further object of the invention therefore relates to a method for precipitating mixed mono or multiple layers of organophosphoric acids of the general formula I (A)

Y—B—OPO$_3$H$_2$           (IA)

and/or of organophosphonic acids of the general formula I (B)

Y—B—PO$_3$H$_2$            (IB)

and the salts thereof, on substrate surfaces of pure or mixed oxides, nitrides or carbides of metals and semiconductors, wherein B is an alkyl, alkenyl, alkinyl, aryl, aralkyl, hetaryl or hetarylalkyl residue and Y is hydrogen or a functional group from the hydroxy, carboxy, amino, optionally low-alkyl-substituted mono or dialkylamino series, thiol, or a negative acid group from the ester, phosphate, phosphonate, sulfate, sulfonate, maleimide, succinimydyl, epoxy, acrylate series, wherein a biological, biochemical or synthetic recognition element may be coupled to B or Y by addition or substitution reaction, wherein compounds may also be added conferring on the substrate surface a resistance to protein adsorption and/or to cell adhesion and in the B chain may optionally be comprised one or more ethylene oxide groups, rather than one or more —CH2— groups, characterized in that water-soluble salts of a compound of formula (IA) or (IB) are used for the treatment of these surfaces, in particular as surfaces of sensor platforms, implants and medical accessory devices.

It is preferred in turn that before precipitation of said mixed monolayers or multiple layers the water-soluble salt of a compound of formula (IA) and/or (IB) is isolated.

Also in the case of mixed SAMs the method according to the invention comprises the said monolayers and multiple layers of compounds of formula (IA) and/or (IB) being free of organic solvents.

Here too it is preferred that sodium, potassium or ammonium salts in particular be used as salts of compounds of formula (IA) and/or (IB).

Also suitable for this embodiment of the method according to the invention are oxides, nitrides or carbides of tantalum, niobium, titanium, vanadium, zirconium, hafnium, molybdenum, tungsten, silicon or mixtures thereof in the form of solid bodies or as layers on substrates of any kind.

A preferred embodiment of the method according to the invention for precipitating mixed monolayers or multiple layers comprises using for the coating compounds of formula (IA) and/or (IB), wherein the B and Y groups are both an alkyl group or an optionally substituted alkyl group of 2-24 C atoms.

It is in turn especially preferred for biosensor applications that materials for biochemical, biological or synthetic recognition elements (coupled to B or Y) be selected from among the group of nucleic acids, such as DNA, RNA, oligonucleotides, nucleic acid analogs, such as PNA, monoclonal or polyclonal antibodies, peptides, enzymes, aptamers, synthetic peptide structures, soluble membrane-bound proteins and proteins isolated from a membrane, such as receptors, ligands thereof, antigens for antibodies, biotin, "histidine tag components" and complexing partners thereof.

It is especially preferred, however, also for applications of the method according to the invention for biologically compatible surface modification of implants that a biologically effective recognition element comprises peptides, proteins, glycoproteins, growth factor, such as TGF-β, or BMP (bone morphogenic protein).

Using the method according to the invention for precipitating mixed monolayers or multiple layers, it is also possible to produce strongly hydrophobic surfaces which can be passivated for example by contact with albumins (for example, human serum albumin (HSA) or bovine serum albumin (BSA)) to achieve a protein-resistant surface.

For this purpose it may in turn be advantageous to add to B or Y a compound which confers on the substrate surface a resistance to protein adsorption and/or cell adhesion, wherein this compound is preferably selected from the group of compounds which are formed from oligo(ethylene oxide), phosphoryl choline, heparin, saccharides, albumins, especially bovine serum albumin or human serum albumin, casein, nonspecific, polyclonal or monoclonal, heterologous or for the analyte or analytes to be determined empirically nonspecific antibodies (especially for immunoassays), detergents (such as Tween 20), fragmented natural DNA or synthetic DNA not hybridizing with polynucleotides for analysis, such as a herring or salmon sperm extract (especially for polynucleotide hybridization assays), or also uncharged, but hydrophilic polymers, such as polyethylene glycols or dextrans.

It is also possible that compounds of formula (IA) and/or (IB) comprise various functional groups and/or biological or biochemical or synthetic recognition elements and/or compounds for conferring on the surface a resistance to protein adsorption and/or cell adhesion in the same SAM molecule.

The substrates may in turn show a smooth surface with low roughness or possess rough surfaces, wherein these surfaces may optionally show additional structuring.

A particular characteristic of the method according to the invention for producing mixed SAMs is that is creates the opportunity to control the hydrophilicity or hydrophobicity of the surface by selecting the ratio of the mixture. This opens up the possibility of a controlled adjustment of surface wettability (contact angle with water). Wettability is an important characteristic in the field of biocompatibility. For certain applications it may be advantageous to set a medium contact angle. As an example of this, the production and characterization of a mixed SAM from dodecyl phosphate/co-hydroxy-dodecyl phosphate is described hereinbelow (see Example 1).

A further characteristic is that a controlled density of positive and/or negative charges on the surface can be achieved by selecting the ratio of the mixture. Surface charge plays an important role with regard to the interaction with biological cells (J. E. Davies, B. Causton, Y. Bovell, K. Davy, C. S. Sturt, "The Migration of Osteoblasts Over Substrata of Discrete Surface-Charge", *Biomaterials*, Vol. 7 (1986), 231-233; R. M. Shelton, I. M. Whyte, J. E. Davies, "Interaction between Primary Bone Cell and Biomaterials. Part 4: Colonization of Charged Polymer Surfaces", *Biomaterials and clinical applications: proceedings of the Sixth European Conference on Biomaterials*, Bologna, Italy, Sep. 14-17, 1986; Elsevier (1987), 597-602). Suitable systems are, for example: Organophosphates or organophosphonates with a terminal amine group (positively charged at a body pH of 7.4) or organophosphates or organophosphonates with a co-terminal negatively charged chemically functional group, such as phosphate or phosphonate, sulfate or sulfonate, carboxylate, etc.

The method according to the invention also enables a controlled density of reactive groups and/or biochemical recognition elements or biological "functions" to be achieved by selecting the ratio of the mixture.

Since selective adsorption properties are observed when using aqueous solutions of organophosphates or organophosphonates (see Example 1), this method permits the production of surfaces which are coated only locally with the SAM while other zones of the surface remain uncoated to be manufactured in a single step.

A further object of the invention is therefore to produce chemically structured surfaces by local precipitation of monolayers or multiple layers of organophosphates and/or organophosphonates on substrate surfaces of pure or mixed oxides, nitrides or carbides of metals or semiconductors, comprising the use of aqueous saliniform compounds of the corresponding organophosphoric acid or organophosphonic acid for the treatment of surfaces and precipitating the pure or mixed monolayers or multiple layers using one of the embodiments of the method mentioned hereinbefore.

In particular, silicon dioxide shows almost no tendency for adsorption of organophosphates or organophosphonates from aqueous solution. Chemically structured surfaces, such as can be manufactured e.g by lithographic or other mask techniques, may thus be used for specific production of surfaces which show specifically differing chemical properties (see Example 1). This technique is useful both for the chemical structuring of biomaterial or implant surfaces, in order e.g. to achieve local control of the adsorption of proteins and growth factors or the adhesion of cells and thus exert an influence on the specific response of the biological environment (in vitro or in vivo) on the surface of the foreign material, and also for structuring the surfaces of biosensors with corresponding locally modifiable properties.

A preferred variant of the method comprises the substrate surface showing a defined pattern with silicon dioxide or transition metal oxides. A further development of this variant comprises a further precipitation of mono- or multiple layers of organophosphates and/or organophosphonates from organic solvents on the silicon dioxide areas.

Finally, the technique is suitable for the partial coating of parts. This is of interest e.g. in the field of medical implants, where differing requirements are often made on different areas of the implant. For example, dental root implants show zones which come into contact with bony tissue following implantation, whereas other zones of the same implant come into contact with the gingiva. These two zones may be modified with the method according to the invention in such a way that they show a surface composition optimized for the local requirements profile. The different SAM layers may be locally and selectively applied, e.g. by partial immersion, brushing, spreading, imprinting or by inkjet methods.

For application of the mono or multiple layers, especially on planar substrates, there are numerous methods available. It is preferred that the mono or multiple layers are precipitated, optionally in a local selective manner, using a method selected from the group comprising immersion, spreading, brushing, "inkjet spotting", mechanical spotting by means of a stylus, pen or capillary, "micro-contact printing", fluidic contact of the substrate surface with parallel or crossed microchannels, under the influence of pressure differences or electrical or electromagnetic potentials.

A special embodiment of the method according to the invention for producing chemically structured surfaces comprises local hydrophilic or hydrophobic areas being produced by local precipitation of mono or multiple layers of organophosphates and/or organophosphonates on substrate surfaces of pure or mixed oxides, nitrides or carbides of metals or semiconductors and their surrounding substrate surface then being coated with a terminally hydrophobic or hydrophilic monolayer.

A further development comprises one or more monolayers being locally precipitated as described hereinbefore on a chemically structured surface produced by the method according to the invention and double or multiple layers thus being locally produced.

As explained hereinbefore, the precipitation method according to the invention is especially suitable for manufacturing substrate surfaces in two different fields of application. A preferred object of the invention relates to the manufacture of implant surfaces with implants from oxide-coated metals, such as titanium, tantalum, niobium, alloys such as titanium-aluminum-vanadium, titanium-aluminum-niobium, titanium-niobium-zirconium, titanium-niobium-zirconium-tantalum, cobalt-chromium, cobalt-chromium-molybdenum, iron-nickel-chromium, wherein pure or mixed mono or multiple layers of organophosphates and/or organophosphonates are precipitated on the surface according to one of the embodiments mentioned hereinbefore.

A further object of the invention is a method for manufacturing sensor platform surfaces comprising the precipitation of pure or mixed mono or multiple layers of organophosphates and/or organophosphonates on the surface according to one of the embodiments mentioned hereinbefore.

The invention also encompasses an implant with a mono or multiple layer of organophosphates and/or organophosphonates as surface, comprising the production of the surface using a precipitation method according to one of the embodiments mentioned hereinbefore.

The implant according to the invention may be selected from the group of root implants for dental applications, artificial prostheses, such as hip joint stems, balls and sockets, artificial knee joints, osteosynthesis components, such as bone plates, screws, "fixateur exteme", components for the repair of damage in the cranial region ("maxillofacial devices"), components in the field of spinal surgery ("spinal surgery implants"), stents, and cardiac pacemaker components.

Further objects of the invention are medical accessory devices of metals or ceramic with a mono or multiple layer of organophosphates and/or organophosphonates as surface, comprising the production of the surface using a precipitation method according to one of the embodiments mentioned hereinbefore.

Medical accessory devices of metal or ceramic according to the invention may be selected from the group comprising catheters, balloon catheters, endoscopes, components for exogenous, blood-carrying systems, such as cardiovascular machines.

A further object of the invention is a sensor platform with a mono or multiple layer of organophosphates and/or organophosphonates as surface, comprising the production of the surface using a precipitation method according to one of the embodiments mentioned hereinbefore.

The sensory platform preferably comprises at least one array of biological or biochemical or synthetic recognition elements, immobilized in discrete measurement areas, for the specific recognition and/or binding of one or more analytes and/or specific interaction with said analytes.

Numerous possible embodiments of the sensor platform according to the invention comprise the detection of one or more analytes by means of labels selected from the group formed from e.g. luminescence labels, especially luminescent intercalators or "molecular beacons", absorption labels, mass labels, especially metal colloids or plastic beads, spin labels, such as ESR or NMR labels, or radioactive labels.

A possible variant comprises detection of the analyte based on the determination of a change in the effective refractive index as a result of molecular adsorption or desorption on the measurement areas.

A sub-variant comprises the detection of analyte based on the determination of a change in the conditions for generating a surface plasmon in the metal layer of a multiple layer system, wherein the metal layer preferably comprises gold or silver.

A preferred embodiment of the sensor platform according to the invention comprises the detection of analyte based on the determination of a change in one or more luminescences.

A possible variant comprises delivering the excitation light in a vertical illuminator.

Depending on the specific embodiment, variants are preferred which comprise the material of the sensor platform that is in contact with the measurement areas being transparent or absorbent within a depth of at least 200 nm from the measurement areas in at least one excitation wavelength.

Another possible embodiment is designed in such a way that the excitation light is delivered in a transmission configuration. For this embodiment, the material of the sensor platform has to be transparent in at least one excitation wavelength.

A preferred embodiment of the sensor platform according to the invention comprises the sensor platform being formed as an optical waveguide which is preferably essentially planar.

The sensor platform is preferably an optically transparent material from the group comprising silicates, e.g. glass or quartz, transparent thermoplastic or moldable plastic, for example polycarbonate, polyimide, acrylates, especially polymethylmethacrylate, or polystyrene.

An especially preferred embodiment of the sensor platform according to the invention comprises an optical thin-layer waveguide with a layer (a) which is transparent in at least one excitation wavelength on a layer (b) which is likewise transparent in at least this excitation wavelength with a lower refractive index than layer (a).

Various embodiments of such sensor platforms and methods for the detection of one or more analytes using such sensor platforms are described in detail for example in patents U.S. Pat. Nos. 5,822,472, 5,959,292 and 6,078,705 as well as in patent applications WO 96/35940, WO 97/37211, WO 98/08077, WO 99/58963, PCT/EP 00/04869 and PCT/EP 00/07529. The herein described embodiments of sensor platforms whose surface has been modified according to the method of the invention and of methods for the detection of one or more analytes using such modified sensor platforms are likewise the object of the present invention.

A further object of the invention is a method for the simultaneous qualitative and/or quantitative detection of numerous analytes comprising one or more liquid samples to be tested for said analytes being brought into contact with the measurement areas on a sensor platform according to the invention and the resulting changes in signals from the measurement areas being measured.

The detection of analytes is preferably based on determining the change in one or more luminescences.

A possible embodiment of the method according to the invention comprises delivering the excitation light from one or more excitation light sources in a vertical illuminator.

Another possible embodiment comprises delivering the excitation light from one or more excitation light sources in a transmission configuration.

The sensor platform is preferably formed as an optical waveguide which is preferably essentially planar, and the excitation light from one or more light sources is preferably coupled into the optical waveguide using a method selected from the group comprising butt joint coupling, coupling via suitable optic fibers as optical waveguides, prism coupling, grating coupling or evanescent coupling by overlapping of the evanescent field of said optical waveguide with the evanescent field of a further waveguide brought into near-field contact therewith.

The addition of one or more samples and of the detection reagents to be used in the method of detection may take place sequentially in several steps. One or more samples are preferably incubated beforehand with a mixture of the various detection reagents for determining the analytes to be detected in said samples and these mixtures then added in a single step to the arrays set up for this purpose on the sensor platform.

A further object of an embodiment of the method according to the invention is the calibration of luminescences generated by the coupling of one or more analytes or by the specific interaction with one or more analytes in the near field of layer (a) comprising the addition of one or more calibration solutions with known concentrations of said analytes to be determined to the same or different measurement areas or segments of measurement areas or arrays of measurement areas on a sensor platform to which one or more of the samples to be tested are added in the same or in a separate step.

An object of the invention is a method according to one of the embodiments mentioned hereinbefore for simultaneous or sequential, quantitative or qualitative determination of one or more analytes from the group of antibodies or antigens, receptors or ligands, chelators or "histidine tag components", oligonucleotides, DNA or RNA strands, DNA or RNA analogs, enzymes, enzyme cofactors or inhibitors, lectins and carbohydrates.

Possible embodiments of the method comprise the samples to be tested being naturally occurring body fluids such as blood, serum, plasma, lymph or urine or egg yolk or optically turbid fluids or tissue fluids or surface water or soil or plant extracts or biological or synthetic process broths or being taken from biological tissue parts or from cell cultures or extracts.

A further object of the invention is the use of a sensor platform according to the invention and/or an analytical system according to the invention and/or a method according to the invention for quantitative or qualitative analysis for the determination of chemical, biochemical or biological analytes during screening procedures in pharmaceutical research, combinatorial chemistry, clinical and preclinical development, for real-time binding studies and for the determination of kinetic parameters in affinity screening and in research, for qualitative and quantitative determination of analytes, especially for DNA and RNA analysis, for the performance of toxicity studies, and for the determination of gene or protein expression profiles, as well as for the detection of antibodies, antigens, pathogens or bacteria in pharmaceutical product development and research, human and veterinary diagnosis, agrochemical product development and research, symptomatic and presymptomatic crop diagnosis, for patient stratification in pharmaceutical product development and for the therapeutic selection of medicines, for the detection of pathogens, noxae and germs, especially salmonellae, prions, viruses and bacteria, in food analysis and environmental analysis.

Embodiments of the invention are illustrated in the following examples.

EXAMPLE 1

Manufacture of Dodecylphosphate SAM and Hydroxydodecylphosphate SAM as Well as Mixed SAMs on Metal Oxide Substrates from Aqueous Solution of the Corresponding Ammonium Salts 1.1 Objective and Specification The aim of this example is to show that the use of ammonium salts of alkyl phosphates in aqueous solution according to the invention permits the specific modification of various oxidic surfaces. The example of the ammonium salt of hydroxy-terminated dodecylphosphoric acid further shows that the invention also permits the production of well-defined SAMs with terminally functionalized alkyl phosphates. It is further shown that the use of mixtures of different alkyl phosphates permits the specific and "stepless" fine adjustment of surface conditions, which is of decisive importance for functionalizing the surfaces both of sensor platforms ("biosensor chips") and of implants and for the functionality thereof.

1.2 Materials and Methods 1.2.1 Substrates $Ta_2O_5$, $Nb_2O_5$: small glass plates (15×15×1 mm) were coated with a 150-nm thick layer of $Ta_2O_5$ or $Nb_2O_5$ (Balzers AG, Balzers, Liechtenstein).

$Ti_{0.4}Si_{0.6}O_2$, $Fe_2O_3$, $ZrO_2$, $SiO_2$: AF45 glass substrates (8×12×1 mm) were coated with a 200-nm thick $Ti_{0.4}Si_{0.6}O_2$ coat. For the tests on $Fe_2O_3$, $ZrO_2$ and $SiO_2$ surfaces, an additional layer (thickness: 14 nm) of the corresponding metal oxide was deposited as outermost layer (Microvacuum, Ltd., Budapest, Hungary).

$TiO_2$: glass substrates were coated by sputtering with a 100 nm thick layer of $TiO_2$ (Paul Scherrer Institute, Villigen, Switzerland).

$Al_2O_3$: Al samples (99.9% purity) of 1 mm thickness were anodized at 25 V in a junction electrolyte, which leads to an oxide layer thickness of about 30 nm (Alusuisse Technology Center, Neuhausen am Rheinfall, Switzerland).

1.2.2 Alkyl Phosphates a) $DDPO_4(NH_4)_2$:

Precipitation of Ammonium Salt 2.00 g dodecylphosphate ($DDPO_4$) (technical quality, Aldrich) was dissolved in 200 ml of 2-propanol (UVASOL, Merck), heated to 82° C. and boiled under reflux. Then 6 ml of ammonia (25% aq., reagent grade, Merck) was added. After cooling in ice water, the precipitated ammonium salt of DDP was filtered, washed with ice water and dried at 60° C. and 10 mbar vacuum for 20 h. 61 g of a white powder (m.p: 225°) was isolated, which corresponds to a yield of 71%.

Control by Means of $^1$H-NMR (DMSO or $CD_3OD$): 0.88 ppm (t, 3H, $-(CH_2)_nCH_3$), 1.28 ppm (m, 18H, $-CH_2CH_2(CH_2)_9CH_3$), 1.54 ppm (m, 2H, $-CH_2CH_2(CH_2)_9CH_3$), 3.72 ppm (q, 2H, $-OCH_2CH_2(CH_2)_9CH_3$), 4.9 (s, 8H, $NH_4$). The $^{31}$P-NMR comprises a single peak, which suggests a pure compound.

Elemental Analysis

Calculated as monoammonium salt: [C] 50.87%, [H] 10.67%, [N] 4.94% [O] 22.59%, [P] 10.93%. Experimental analysis: [C] 50.61%, [H] 10.94%, [N] 4.95% [O] 22.75%, [P] 10.69%.

b) $OH-DDPO_4(NH_4)_2$:

Precipitation of Ammonium Salt 500 mg of hydroxydodecylphosphate ($OH-DDPO_4$) was dissolved in 20 ml of 2-propanol (UVASOL, Merck), and the solution was purged with $NH_3$ gas for 5 minutes. The precipitated ammonium salt of $OH-DDPO_4$ was isolated by centrifugation, washed and dried in a stream of dry nitrogen gas. 515 mg of white powder was isolated (yield: 91%).

Control by Means of $^1$H-NMR (DMSO or $CD_3OD$): 1.24 ppm (m, 16H, $-CH_2CH_2(CH_2)_8CH_2CH_2OH$), 1.38 ppm (m, 2H, $-CH_2CH_2(CH_2)_8CH_2CH_2OH$), 1.44 ppm (m, 2H, $-CH_2CH_2(CH_2)_{10}OH$), 3.35 ppm (t, 2H, $-(CH_2)_nCH_2OH$), 3.57 ppm (q, 2H, $-OCH_2CH_2(CH_2)_{10}OH$), 5.2 (s, 8H, $NH_4$).

Elemental Analysis

Calculated as diammonium salt: [C] 45.6%, [H] 10.5%, [N] 8.9%. Experimental analysis: [C] 44.1%, [H] 9.6%, [N] 5.7%.

The elemental analysis shows that, in comparison with the diammonium salt, the nitrogen content is somewhat lower than expected. This is probably attributable to a certain loss of ammonia and conversion to the monoammonium salt. It can be concluded from the NMR spectra, which do not contain any nonidentifiable peaks, that there are no impurities in high concentrations.

1.2.3 Preparation of the Treatment Solution

A) 150 mg of $DDPO_4(NH_4)_2$ was dissolved in 5 ml of ultrapure water, the solution being gently heated to 50° C. The volume was made up to 100 ml.

B) 158 mg of $OH-DDPO_4(NH_4)_2$ is dissolved in 5 ml of ultrapure water by heating to about 80° C. The solution was passed through a 0.22 μm filter (MILLEX-GV, MILLIPORE, Bedford, Mass.) and the volume made up to 100 ml.

The two solutions a) and b) were mixed in various ratios, from 0 to 100% by volume in relation to $OH-DDPO_4(NH_4)_2$. 11 different solutions, whose content of $OH-DDPO_4(NH_4)_2$ was increased in each case by 10%, were prepared. The total content of phosphate was maintained at a constant 0.5 mM.

1.2.4 Sample Treatment

The substrates for the surface modification tests were cleaned upon sonication for 15 min in ultrapure water and then for 15 min in 2-propanol. After drying, they were subjected for 3 min to oxygen-plasma cleaning (Harrick Plasma Cleaner/Sterilizer PDC-32G, Ossining, N.Y., USA). They were then transferred to a glass vessel, to which the aqueous solution of alkyl phosphate was then added. After treatment for 48 h, the samples were taken, rinsed with water and dried in a stream of nitrogen.

1.3 Results a) $DDPO_4$ on Various Substrates

The alkyl phosphates were applied to the following surfaces: $Al_2O_3$, $Ta_2O_5$, $Nb_2O_5$, $ZrO_2$, $Fe_2O_3$, $TiO_2$, $Ti_{0.4}Si_{0.6}O_2$ and $SiO_2$. Treatment was carried out in 0.5 mM $DDPO_4(NH_4)_2$, as described in the previous section.

1. Contact Angle

The advancing contact angles are summarized in Table 1. Results show that highly hydrophobic, self-assembled monolayers are formed on all metal oxides. A contact angle of greater or equal 110° is typical of perfect SAMs. Exceptions are silicon dioxide ($SiO_2$) and $TiO_{0.6}SiO_4O_2$. The isolelectric point does not play any visible role here; it varies from 2.7-3.0 for $Ta_2O_5$ to 7.0-8.6 for $Fe_2O_3$ (Table 1). On the $SiO_2$-surface the contact angle remains within the limits of the values prior to treatment, i.e. the surface remains completely hydrophilic. It is thus clear that this surface does not react with the alkyl phosphates and does not form a SAM.

The $Ti_{0.4}Si_{0.6}O_2$ layer on the glass chips comprises a heterogeneous structure of $TiO_2$ and $SiO_2$. The $Ti_{0.4}Si_{0.6}O_2$ surfaces form an incomplete DSAM in the treatment solution, wherein the contact increases, but only values of about 64° are reached. This correlates with the observation that while SAMs are formed on $TiO_2$, they are not formed on $SiO_2$.

TABLE 1

Literature values of isoelectric points (IEP) of metal oxides used, experimentally measured contact angle (CA) after treatment with aqueous $DDPO_4(NH_4)_2$ solution, and droplet density (DD) measured after formation of the condensation figures on the same surfaces treated with $DDPO_4(NH_4)_2$; (SD = standard deviation).

| Substrates | IEP | Ref (IEP) | CA (± SD) | DD (± SD) |
|---|---|---|---|---|
| $Ta_2O_5$ | 2.7-3.0 | 14 | 114.6 ± 0.48 | 129 ± 19 |
| $Al_2O_3$ | 7.5-8.0 | 15 | 111.4 ± 1.07 | 152 ± 22 |
| $Nb_2O_5$ | 3.4-3.6 | 16 | 109.7 ± 0.63 | 120 ± 18 |
| $ZrO_2$ | 4.0 | 17 | 110.1 ± 0.61 | 258 ± 39 |
| $Fe_2O_3$ | 7.0-8.6 | 18/19 | 110.8 ± 0.64 | 197 ± 30 |
| $Ti_{0.4}Si_{0.6}O_2$ | 3.6 | 20 | 63.8 ± 1.93 | 334 ± 50 |
| $TiO_2$ | 4.7-6.2 | 21 | 111.4 ± 1.18 | 221 ± 33 |
| $SiO_2$ | 1.8-2.2 | 22 | 10.0 ± 3.42 | >3000 |

2. Droplet Density $DDPO_4$ SAMs on the pure metal oxides show, after formation of the condensation film, a very low droplet density of 120-260 droplets/mm$^2$ (Table 1) and a homogeneous distribution of droplets over the surface. SiO$_2$ remains hydrophilic, and a continuous water film is formed, because the high density of droplets rapidly leads to coalescence. On the Ti$_{0.4}$Si$_{0.6}$O$_2$ surface coated with DDPO$_4$, a DD of about 350 dropöets/mm$^2$ forms. This value, as expected, is higher than on the pure metal oxide surfaces which form SAMs and suggests an incomplete SAM formation.

By means of precipitation from the gas phase, Fe$_2$O$_3$ was applied in the form of 2 mm wide strips to glass chips coated with Ti$_{0.4}$Si$_{0.6}$O$_2$. During the rinsing process after coating in the DDPO$_4$ solution it became obvious that only the Fe$_2$O$_3$ zones became hydrophobic, whereas the adjacent Ti$_{0.4}$Si$_{0.6}$O$_2$ zones remained hydrophilic. The observed 2 mm wide water-repellent strips in FIG. 4 correspond to the Fe$_2$O$_3$ zone.

3. X-Ray Photoelectron Spectroscopy

After immersion of the metal oxide and silicon dioxide sample surfaces in a 0.5 mM aqueous DDPO$_4$(NH$_4$)$_2$ solution, the surfaces were analyzed by x-ray photoelectron spectroscopy (XPS) in two different exit angles. At an electron exit angle of 15° (in relation to the surface) the XPS analysis is highly surface-sensitive, whereas at an angle of 75° deeper zones (substrate) are also included in the analysis.

The concentrations of C, O, P and of the corresponding metal oxide cations were quantified by means of standard sensitivity factors (Table 2a and b).

The quantity of the SAM analyzed lies in the same range for all metal oxides studied and suggests a monolayer surface occupancy. In conformity with the measurements of contact angle and droplet density, no SAMs were observed on the SiO$_2$ samples (no phosphorus signal and comparatively little carbon). On the mixed layer (Ti$_{0.4}$Si$_{0.6}$O$_2$) about half as much titanium is detected as on the pure titanium dioxide (TiO$_2$) layer. Accordingly, only about half the concentrations of P and C are found compared with the corresponding TiO$_2$ surface. This in turn demonstrates that the SAM only forms on TiO$_2$, but not on SiO$_2$.

TABLES 2a and b

Atomic concentrations measured by XPS of metal oxide substrates coated with DDPO$_4$. Electron exit angle: 15° and 75° in relation to the surface. The values in parentheses correspond to the atomic concentrations of titanium from the substrate under the sputter-coated Fe$_2$O$_3$ sample, or to the atomic concentration of silicon in the case of the Ti$_{0.4}$Si$_{0.6}$O$_2$ sample.

| Substrate MO$_x$ | % C | % O (tot) | % M | % P |
|---|---|---|---|---|
| Atomic concentrations (15° exit angle) | | | | |
| Ta$_2$O$_5$ | 67.8 | 23.2 | 6.71 | 2.36 |
| Al$_2$O$_3$ | 67.6 | 21.1 | 8.85 | 2.53 |
| Nb$_2$O$_5$ | 59.7 | 29.6 | 8.5 | 2.26 |
| ZrO$_2$ | 72.2 | 22.0 | 3.06 | 2.77 |
| Fe$_2$O$_3$ | 66.1 | 27.5 | Fe: 3.09/Ti: 0.41 | 2.86 |
| TiO$_2$ | 68.6 | 23.0 | 6.13 | 2.23 |
| SiO$_2$ | 6.2 | 70.8 | 22.9 | 0 |
| Ti$_{0.4}$Si$_{0.6}$O$_2$ | 26.2 | 54.5 | Ti: 3.04/Si: 15.1 | 1.13 |
| Atomic concentration (75° exit angle) | | | | |
| Ta$_2$O$_5$ | 27.3 | 53.7 | 17.4 | 1.61 |
| Al$_2$O$_3$ | 25.3 | 47.1 | 25.5 | 2.10 |
| Nb$_2$O$_5$ | 31.9 | 49.4 | 17.3 | 1.30 |
| ZrO$_2$ | 35.9 | 49.0 | 12.9 | 2.28 |
| Fe$_2$O$_3$ | 28.9 | 56.5 | Fe: 10.2/Ti: 2.46 | 1.93 |
| TiO$_2$ | 31.2 | 49.4 | 17.6 | 1.83 |
| SiO$_2$ | n.b.[a] | n.b.[a] | n.b.[a] | n.b.[a] |
| Ti$_{0.4}$Si$_{0.6}$O$_2$ | 14.9 | 60.2 | Ti: 9.97/Si: 14.1 | 0.85 |

[a] not observed b) OH-DDPO$_4$ on Ta$_2$O$_5$ and Nb$_2$O$_5$

Self-assembled layers of 12-hydroxydodecylphosphate (OH-DDPO$_4$) on samples coated with Ta$_2$O$_5$ and Nb$_2$O$_5$ were prepared by immersion in an aqueous solution of 0.5 mM OH-DDPO$_4$(NH$_4$)$_2$, as described in the experimental section (see above).

1. Contact Angle and XPS

The advancing contact angle was measured immediately after surface treatment of the samples. It amounts to about 50°, i.e. the surface is strongly hydrophilic compared with the methyl-terminated layer of DDPO$_4$, but less hydrophilic than the cleaned metal oxide surface (contact angle <10°).

This is a clear indication that the hydroxy groups on the surface are actually exposed. To prove this, XPS spectra were measured at different exit angles. The variation of signal intensity as a function of exit angle enables evidence to be obtained on the position of the corresponding element. The O(1s) signal is shown in FIG. 5 for the two different exit angles 11.5° and 20.5°. Compared with the pure DDPO$_4$ layer, the oxygen signal (O1s) shows an additional shoulder at a binding energy of 533.4 eV (FIG. 5), the intensity being significantly higher at 11.5° than at 20.5°. The position of the O(1s) signal here is typical of hydroxy functions.

No nitrogen was detected, indicating that the ammonium cation does not participate in the formation of the SAM on the surfaces studied here.

It has already been shown that the water contact angle correlates with the level of SAM occupancy. Contact angles of hydroxy-terminated SAMs were measured at 50-80°. To test whether hydroxy-terminated alkyl phosphates form a densely packed layer similar to DDPO$_4$, the XPS C1s intensities of the DDPO$_4$ SAMs were compared with those of the OH-DDPO$_4$ SAMs at different exit angles (FIG. 6). The results show that the corresponding C1s signals are closely comparable. This demonstrates that hydroxy-terminated alkyl phosphate (OH-DDPO$_4$) forms layers also forms densely packed layers as those they are typical of organized SAMs.

The atomic concentrations of C, O, P and of the substrate cation Ta or Nb were calculated from the corresponding XPS intensities (Table 3). The data are consistent with the model of a surface on which the phosphates are bound to the metal oxide, whereas the terminal groups (hydroxy and methyl) point away from the surface ("tail-up" configuration).

The O1s oxygen signals were deconvoluted into three components: a) the metal oxide oxygen (530.2 eV), by the phosphate oxygen (531.4 eV for P—O metal and P=O and 532.6 eV for R—O—P and P—OH), and c) the hydroxide oxygen (OH) at 533.4 eV. This assignment is based on a corresponding detailed analysis of the XPS spectra. The data confirm that not only pure alkyl phosphate, but also OH-DDPO$_4$ binds to the surface in an aligned manner (FIG. 7).

The increase in the oxygen signal of the metal oxide substrate with the increasing angle of detection is caused by the increasing information depth of the method (maximum analyzed depth at perpendicular (90°) detection). The oxygen signal of the phosphate group decreases slightly with an increasing angle of detection. This is typical of elements located at the boundary surface. The oxygen signal of the hydroxy group increases slightly with a decreasing angle of detection, which is typical of a hydroxy group position at the boundary surface of SAM/air or vacuum.

TABLES 3a and b

XPS atomic concentrations of self-assembling OH-DDPO$_4$ layers on Ta$_2$O$_5$ and Nb$_2$O$_5$ as a function of the angle of detection Θ used. The oxygen signal was deconvoluted into three components.

| Angle of detection Θ | Sin Θ | Atom-% Ta | Atom-% O | Atom-% P | Atom-% C |
|---|---|---|---|---|---|
| 11.5 | 0.20 | 3.05  | 26.6 | 3.69 | 66.72 |
| 20.5 | 0.35 | 6.27  | 33.0 | 3.91 | 56.79 |
| 30.0 | 0.50 | 9.21  | 39.8 | 3.12 | 47.78 |
| 40.5 | 0.65 | 11.9  | 45.8 | 2.83 | 39.46 |
| 53.1 | 0.80 | 13.42 | 50.3 | 2.00 | 34.29 |
| 71.8 | 0.95 | 14.88 | 53.3 | 2.12 | 29.65 |

| Angle of detection Θ | Sin Θ | Atom-% Nb | Atom-% O | Atom-% P | Atom-% C |
|---|---|---|---|---|---|
| 11.5 | 0.20 | 4.64  | 29.3 | 3.86 | 62.21 |
| 20.5 | 0.35 | 6.74  | 33.9 | 3.32 | 55.97 |
| 30.0 | 0.50 | 9.53  | 38.5 | 3.07 | 48.62 |
| 40.5 | 0.65 | 11.97 | 43.6 | 2.78 | 41.97 |
| 53.1 | 0.80 | 14.05 | 47.7 | 2.01 | 36.24 |
| 71.8 | 0.95 | 16.38 | 51.6 | 2.07 | 29.98 | c) Mixed SAMs of OH-DDPO$_4$/DDPO$_4$ on Ta$_2$O$_5$ and TiO$_2$

Mixtures of aqueous solutions of 0.5 mM OH-DDPO$_4$ (NH$_4$)$_2$ and 0.5 mM DDPO$_4$(NH$_4$)$_2$ were prepared as described in the experimental section. Glass chips coated with Ta$_2$O$_5$ were cleaned and treated in the solutions as described in the experimental section.

1. Contact Angle and Droplet Density

The contact angle was measured immediately after preparation of the surfaces. The results (FIG. 8) show a clear correlation with the molar ratio of the mixture of the two SAM components in the solution.

The droplet density is homogeneously distributed over the surface on the macrometer and micrometer scale, so it can be concluded that the two SAM components are homogeneously distributed in this order of magnitude. The difference in wettability (contact angle) has only a minor influence on droplet density (Table 4). An increase in this density is to be expected if the roughness, surface charge and/or disarrangement of the layers increases. The low density of the droplets of 100-200 per mm$^2$ indicates that the layers are relatively well organized and smooth (Tab. 4). The incorporation of OH-DDPO$_4$ into the alkyl phosphate layer thus has no major influence on the degree of organization of the SAMs.

TABLE 4

Contact angle and droplet density of mixed OH—DDPO$_4$/DDPO$_4$ SAM on Ta$_2$O$_5$; (SD = standard deviation).

| Vol-% OH—DDPO$_4$ in solution | Contact angle (±SD) | Droplet density (±SD) |
|---|---|---|
| 0   | 110.1 ± 0.8 | 144 ± 29 |
| 10  | 105.6 ± 1.7 | 126 ± 26 |
| 20  | 103.6 ± 1.0 | 104 ± 21 |
| 30  | 86.6 ± 1.4  | 167 ± 33 |
| 40  | 81.6 ± 1.4  | 125 ± 25 |
| 50  | 73.0 ± 1.8  | 102 ± 21 |
| 60  | 70.9 ± 1.9  | 72 ± 30  |
| 70  | 64.1 ± 2.3  | 161 ± 32 |
| 80  | 58.2 ± 1.5  | 123 ± 25 |
| 90  | 57.3 ± 1.2  | 229 ± 46 |
| 100 | 54.3 ± 3.5  | 159 ± 32 |

1.4 Conclusion

It has been shown that alkyl phosphates from aqueous solutions of corresponding salts (e.g. ammonium salts) form well-defined self-assembling layers ("SAM") on a series of metal oxide surfaces. Using XPS, no nitrogen was detected, thus leading to the conclusion that these SAMs are especially pure, i.e. that they comprise neither the cation of the salt nor organic solvents. Only a certain proportion of water can be expected at the boundary surface. However, this is noncritical both for biomaterial (implant) and for biosensor applications.

In the case of pure alkyl phosphate, highly hydrophobic surfaces could be produced using the method according to the invention. It was shown here that alkyl phosphate selectively forms SAMs on transition metal oxides as well as on aluminum oxide, whereas silicon dioxide is not coated. This opens up the possibility of manufacturing chemically structured surfaces on the millimeter to submicrometer or nanometer scale by applying the treatment method of the invention to chemically structured surfaces (e.g. using microfabrication techniques such as lithography). For example, any photo or electron beam-lithographic sample with surfaces locally comprising silicon (dioxide) or a transition metal oxide or aluminum oxide may be selectively coated with alkyl phosphates or terminally functionalized alkyl phosphates. The silicon dioxide surfaces may in addition be functionalized in a second step using a different method. This also includes the possibility of precipitating on these surfaces alkyl phosphates or functionalized alkyl phosphates from organic solvents, since it is known that silicon dioxide may also be coated from such nonaqueous solutions. Thus, for example, samples with locally hydrophilic/hydrophobic properties may be produced. It is thus also possible to apply locally differing functional groups. These include different charges (use of e.g. positively charged, terminal amino or ammonium groups and negatively charged carboxy, phosphate or phosphonate groups). A further possibility is the local application of protein and cell adhesion-resistant groups (e.g. using alkyl phosphates terminally modified with oligo-ethylene oxide), while other zones of the surface have an adhesive character by showing protein-adsorbing properties. The latter may also be further enhanced by applying in these zones alkyl phosphates which comprise terminally bound cell-adhesive proteins, such as RGD-containing peptides. In this way it is possible to direct proteins and biological cells selectively to certain zones of the surface and to use the specific behavior pattern of such separately applied cells. It is likewise possible for biosensor applications to apply recognition elements, such as antibodies of proteins, single-strand DNA or RNA chains, etc., locally and selectively and thus create the possibility of specifically conducting bioaffinity tests on certain zones of the surface. This is of interest with regard to the "multiarray" technique in sensor technology.

The above descriptions apply by analogy also for salts of alkyl phosphonic acids, whose properties, especially with regard to the modification of metal oxide surfaces, are very similar.

EXAMPLE 2

Manufacture of Dodecylphosphate SAM and Hydroxydodecylphosphate-SAM as Well as Mixed SAMs on Smooth and Rough Metallic Titanium Implant Surfaces 2.1 Objective and Specification This example is intended to show that salts of various alkyl phosphoric or alkyl phosphonic acids in aqueous solution are also applicable for the modification of metallic, oxide-coated implant surfaces using the method according to the invention. It should further be shown that not only smooth (e.g. polished), but also rough, topographically structured surfaces can be successfully treated.

2.2 Materials and Methods

Substrates: Metal probes of cp (commercially pure) titanium which always show a naturally formed titanium oxide layer were treated in two different variants as follows:

A) Mechanical grinding and polishing, subsequent cleaning in the organic solvents hexane, acetone and alcohol, followed by passivation in 30% $HNO_3$ solution and final cleaning in oxygen-plasma. This leads to a clean and smooth surface.

B) Blasting with aluminum oxide particles, followed by chemical etching in chloride-containing sulfuric acid. This leads to a highly roughened surface, as shown on scanning electron microscopy (FIG. 9). Such surfaces are preferably used for implants in the skeletal area, because they show an outstanding capacity for complete integration in the bone ("osseointegration").

2.2.1 Alkyl Phosphates

The same materials were used as in Example 1.

2.2.2 Manufacture of Treatment Solutions and Treatments of Metallic Samples.

The same methods were used as in Example 1.

2.3 Results a) $DDPO_4(NH_4)_2$ and OH-$DDPO_4(NH_4)_2$ on Smooth Titanium Surface Aqueous solutions both of pure $DDPO_4(NH_4)_2$ and pure OH-$DDPO_4(NH_4)_2$ and also different mixture ratios of these two substances were used for the treatment of smooth and rough titanium surfaces.

Table 5 shows the XPS results of the treated surfaces. As in Example 1, these data show that, with the method according to the invention, also metallic titanium surfaces (with oxidic passive layer) are occupied by corresponding molecules in the same way as pure titanium oxide layers.

FIG. 10 shows the corresponding contact angle, measured against water. These are very similar to the correspondingly treated metal oxide-coated surfaces (Example 1). Again a characteristic dependence of the contact angle on the composition of the SAM solution is observed. The method is thus also suitable with these materials for the specific adjustment of surface-relevant properties (in this case wettability).

TABLE 5

Surface concentration of smooth, metallic titanium surfaces, treated according to the method of the invention with aqueous solutions of the salts $DDPO_4(NH_4)_2$, OH—$DDPO_4(NH_4)_2$ or mixtures thereof in different concentration ratios.

| Vol-% OH—$DDPO_4$ in solution | Atomic concentrations (90° exit angle) | | | |
|---|---|---|---|---|
| | % C | % O (total) | % Ti | % P |
| 0 | 46.66 | 36.59 | 13.76 | 3 |
| 10 | 55.81 | 31.06 | 10.16 | 2.98 |
| 20 | 57.03 | 30.49 | 9.62 | 2.86 |
| 30 | 48.11 | 36.73 | 12.24 | 2.92 |
| 40 | 49.01 | 36.55 | 12 | 2.44 |
| 50 | 54.31 | 32.49 | 10.27 | 2.93 |
| 60 | 47.06 | 37.86 | 12.61 | 2.47 |
| 70 | 49.28 | 36.07 | 12.1 | 2.55 |
| 80 | 49.81 | 35.94 | 11.82 | 2.43 |
| 90 | 49.66 | 36.58 | 11.84 | 1.92 |
| 100 | 45.63 | 39.32 | 12.36 | 2.68 | b) $DDPO_4(NH_4)_2$ and OH-$DDPO_4(NH_4)_2$ on Rough Titanium Surface

Table 6 shows the XPS data of the metallic rough surfaces treated with aqueous solutions of the salts $DDPO_4(NH_4)_2$ and OH-$DDPO_4(NH_4)_2$ or mixtures thereof. These samples show a surface structure as illustrated in FIG. 9. Again the surface concentrations indicate a complete formation of the corresponding SAMs. The concentrations here differ slightly from those of smooth surfaces, which is attributable to the influence of surface topography on the XPS measurement.

FIG. 11 shows the corresponding contact angles as in FIG. 10. The contact angles here show a markedly different course compared with the corresponding curves for smooth surfaces. This is attributable to the influence of surface topography. It is known that rough (topographically structured), hydrophobic surfaces show markedly higher contact angles (reduced wetting) than smooth hydrophobic surfaces (Ref). This effect is also observed in nature, and it is from these observations that the name Lotus Effect derives, because, for example, lotus leaves use precisely this combination of roughness and hydrophobicity to form a self-cleaning surface.

The high contact angles of the surface treated with $DDPO_4(NH_4)_2$ unequivocally show that these rough surfaces are perfectly coated with the $DDPO_4$-SAM.

TABLE 6

Surface concentration of rough, metallic titanium surfaces, treated according to the invention with aqueous solutions of the salts $DDPO_4(NH_4)_2$, OH—$DDPO_4(NH_4)_2$ or mixtures thereof in different concentration ratios.

| Vol-% OH—$DDPO_4$ in solution | Atomic concentrations (90° exit angle) | | | |
|---|---|---|---|---|
| | % C | % O (total) | % Ti | % P |
| 0 | 42.64692 | 38.87785 | 15.28833 | 3.186893 |
| 10 | 42.01745 | 39.3542 | 14.94158 | 3.686767 |
| 20 | 42.21079 | 39.2392 | 14.57747 | 3.972532 |
| 30 | 41.14441 | 40.02102 | 14.01979 | 4.814779 |
| 40 | 41.1987 | 41.81364 | 13.49958 | 3.488083 |
| 50 | 42.50703 | 40.95192 | 12.98231 | 3.55874 |
| 60 | 41.44062 | 42.45984 | 12.19712 | 3.902415 |
| 70 | 42.90176 | 40.70315 | 12.57557 | 3.819517 |
| 80 | 42.77291 | 40.86229 | 12.66196 | 3.702839 |
| 90 | 41.26897 | 40.97354 | 13.70276 | 4.054732 |
| 100 | 42.8869 | 40.12049 | 13.88565 | 3.106954 |

It is thus shown that not only smooth titanium surfaces, but also those with a large specific surface and complex roughness, as often used for implants, e.g. for bone implants, can be successfully coated according to the method of the invention.

EXAMPLE 3

Sandwich Immunoassays on Sensor Chips Coated with DDP: Quantitative Determination of the Analytes Immunoglobulin (Rabbit IgG) and the Human Cytokine Interleukin 6 (hIL-6) by Fluorescence Detection on Planar Waveguides as Sensor Platform The aim of the experiments was to show that surface modification of a planar thin-layer waveguide as sensor platform according to the invention by the application of monolayers of alkyl phosphates or phosphonates can produce a marked increase in sensitivity compared with sensor platforms which have not undergone such pretreatment according to the invention. The detection sensitivity thus achieved lies in the lower pg/ml range. Such sensitivity can only be achieved if a correspondingly large number of recognition antibodies can be applied to the sensor surface in active form, i.e. without denaturation. This may be achieved by applying a dodecylphosphate SAM (DDP-SAM). Furthermore, it should be demonstrated that assays on sensor chips without prior precipitation of a DDP monolayer, but otherwise with the same pretreatment, show correspondingly lower assay signals. Furthermore, it should be shown that a monolayer of DDP and thus the number of surface-bound recognition molecules remains stable over the course of an experiment of several hours and also that it does not suffer damage as a result of additional mechanical stress, e.g. as a result of vigorous rinsing of the surface with measuring buffer. The stability manifests itself by a constant fluorescence signal response following a binding experiment.

3.1. Sensor Platforms

Rectangular, planar waveguide chips comprising a thin highly refractive waveguide layer on a 0.7 mm thick transparent substrate with the outer dimensions of 16 mm high×48 mm wide×0.7 mm thick were used as sensor platforms. The optically transparent substrate material of the sensor chip comprised AF45 glass (refractive index n=1.52 at 633 nm). In the substrate were five surface relief gratings with a width of 0.5 mm (in the direction of propagation of the excitation light to be coupled into the layer of the sensor platform via the grating structure) and structured along the full height (48 mm) of the substrate. The gratings were arranged at intervals of 9 mm along the breadth of the chip. The area between two gratings was used as measuring surface. The relief gratings showed a period of 360 nm and a depth of 12 nm. The wave-guiding, optically transparent layer comprising $Ta_2O_5$ had a refractive index of 2.11 at 633 nm (layer thickness 150 nm).

The relief gratings serve to couple laser light of a defined wavelength (here 633 nm) into the sensor layer. Light coupled into the sensor layer and guided there is used for the excitation of fluorophores located close to the surface, i.e. fluorophores located in the evanescent field of the guided light. The fluorescence light generated at the surface in this way serves as a measuring signal for the binding of analyte molecules to specific recognition elements immobilized on the sensor surface. The number of bound analyte molecules can be determined from the intensity of the emitted fluorescence.

A flow cell structure was linked to the pretreated sensor platform for contact of the analysis sample with the sensor chip. The flow cell structure comprised sample vessels in each of which there was a measuring surface between two gratings on the chip. Each sample vessel had a volume of 15 µl, with a base area of 7 mm×11 mm on the sensor surface and a cell height of 0.2 mm. The analysis sample could be added to or removed from the cell via an injection or drainage channel (diameter 0.5 mm). The sample/buffer was added by means of a dispensing pump via hose connections fitted between the pump and the inlet.

3.2. Chip Pretreatment

Before being joined together with the flow cell structure, the sensor surface was cleaned by means of a wet chemical process first with isopropanol several times, then with concentrated sulfuric acid containing 2.5% ammonium peroxodisulfate. A monomolecular layer (monolayer) of dodecylphosphate (DDP) was then precipitated on the hydrophilic waveguide surface from aqueous phase in a self-assembly process. A 0.5 mM DDP/ammonium salt solution in water was used for the precipitation. The sensor surface was incubated for 2 h in the DDP solution under constant agitation at room temperature, then thoroughly washed in running water and dried under a stream of nitrogen. The precipitation of the DDP monolayer led to a hydrophobic surface (contact angle about 110° with water).

3.3. Application of Biological Recognition Elements (A) For Detection of Rabbit IgG The sensor surface was incubated with an aqueous solution of biotinylated bovine serum albumin (BSA-biotin, Sigma, catalog no. A-6043). A 100 µg/ml solution in phosphate-buffered saline solution (PBS), pH 7.4, was used. The chip was incubated for 1 h at room temperature, thoroughly washed under running, deionized water (Millipore, spec. resistance=18 mΩ cm) and then dried under a stream of nitrogen. The surface was then blocked using a solution of 1 mg/ml pure bovine serum albumin (BSA, Sigma, catalog no. A7906) in PBS, pH 7.4. Incubation was resumed for 15 min, and the chip was again washed thoroughly under running, deionized Millipore water and then dried under a stream of nitrogen. The blocked chip was then incubated in the same manner with 50 µg/ml streptavidin (Sigma catalog no. S4762) in PBS, pH 7.4, for 30 min. The streptavidin molecules here bind to the available biotin groups of the albumin. Surplus streptavidin was removed again by rising with water. Finally, the surface was incubated with the biotinylated recognition antibody anti-rabbit IgG (Sigma, catalog no. B-7389) in a concentration of 12 µg/ml in PBS, pH 7.4, for 30 min, thoroughly washed again and dried with nitrogen. The dry chip was then connected to the flow cell structure.

(B) For Detection of hIL-6

The sensor surface was incubated in the region of the measuring surface with 50 µl of an aqueous solution of monoclonal mouse anti-hIL-6 antibody (R&D Systems, catalog no. mAb206). The freeze-dried mouse anti-hIL-6 antibody was reconstituted in a concentration of 0.5 mg/ml in ten percent, phosphate-buffered saline solution (10% PBS), pH 7.4, and then diluted with 10% PBS, pH 7.4, to a concentration of 10 µg/ml. With this solution, the chip was incubated for 2 h at room temperature, thoroughly washed under running, deionized Millipore water (spec. resistance=18 mΩ cm) and then dried under a stream of nitrogen. The surface was then blocked using a solution of 1 mg/ml bovine serum albumin (BSA, Sigma, catalog no. A7906) in PBS, pH 7.4. Incubation was resumed for 15 min, and the chip was again washed thoroughly under running, deionized Millipore water and then dried under a stream of nitrogen. The dried chip was connected to the flow cell structure and inserted into the measuring apparatus.

3.4. Analytical Measuring Apparatus

The sensor chip is mounted on a computer-controlled adjustment unit which permits translation parallel with and perpendicular to the grating lines as well as rotation about an axis parallel with the grating lines of the sensor platform. Immediately behind the laser used as excitation light source is a shutter in the light path designed to block this light path when no measurement data are to be recorded. In addition, neutral filters or polarizers may be placed here or also at other positions along the path of the excitation light to the sensor platform to achieve stepped or continuous variations in the intensity of the excitation.

The excitation light beam of a helium neon laser at 632.8 nm (Melles-Griot 05-LHP-901, 1.1 mW) is expanded in one dimension with a lens system using a cylinder lens and directed through a slit aperture measuring 0.5 mm×7 mm to produce a parallel light bundle almost rectangular in cross-section and almost homogeneous in cross-section intensity. Thereby, the polarization of the laser is orientated in parallel with the grating lines of the sensor platform for excitation of the $TE_0$ mode under coupling conditions. The excitation light is directed through the rear aspect of the sensor platform, i.e. through the optically transparent layer (b) onto a in-coupling grating within one of the 5 sample vessels, wherein the in-coupling grating in a sample vessel under the conditions in the example is located on the left margin of the rectangular sample cell. The angle between the sensor platform and the incoming excitation light bundle is adjusted for maximum coupling into the optically transparent layer (a) by rotation about the aforementioned axis. With the aforementioned parameters of the sensor platform, the resonance angle for the in-coupling in air was about 2.6°.

A red-sensitive photomultiplier tube (PMT) (H6240, Hamamatsu, Japan), which is used in single-photon counting mode with a 225 MHz counter (model 53131A, Hewlett-Packard, USA), serves as detector. The signal recording and focusing of the fluorescence light emitted from the substrate side of the sensor chip onto the detection window of the PMT take place using an objective of own construction (imaging ratio 1:1, numerical aperture 0.19). In the parallel section of the light path of the objective, mounted on a filter changer, are two interference filters (Omega, Brattleborough, Vermont) with a central wavelength of 680 nm and 40 nm bandwidth, as well as a thin glass plate in front of the filter unit as beam splitter, which can detect excitation light emitted from the sensor surface as a reference signal via measurement with a photodiode. This arrangement ensures that the luminescence signal and the reference signal originate from the same measuring range. The reference signals (at the excitation wavelength) and the actual measuring signal (at the luminescence wavelength) can be measured simultaneously. The measuring signals displayed have already been corrected by means of the reference signal in order to eliminate variations in the measuring range. The measuring signals were determined as a quotient of the luminescence signal and the reference signal, multiplied by the factor $10_6$.

3.5. Performance of the Analytical Detection Method

The sandwich immunoassay format was selected for the specific recognition of the analytes to be detected (rabbit IgG and h-IL-6).

3.5.1. Sample Preparation

Of the analytes to be quantified (rabbit IgG and h-IL-6) standard solutions of 500 µl in PBS, pH 7.4, with 0.1% BSA and 0.05% Tween20 were prepared in each case. The concentrations in each case amounted to 0, 0.067, 0.67, 6.7, 67, and 670 pM for the analyte rabbit IgG (Sigma, catalog no. 1-5006) and 0, 0.5, 1, 2.5, 5, 25, 50, 250, 500, 2500, 10000 pg/ml for the analyte hIL-6 (R&D Systems, catalog no. 206-IL-06) with the addition in each case of 10% calf serum (Anawa, catalog no. 8270-0209). These standard solutions were intended for generating calibration curves of the analytes in order to determine the concentrations of samples of unknown analyte quantity.

The calibration solutions and also the samples with unknown analyte concentrations to be determined were then mixed in each case with 500 µl of a solution comprising polyclonal tracer antibodies. Anti-rabbit IgG from goat, labeled with Cy5-dye (Amersham-Pharmacia, catalog no. PA45004), with a dye-to-protein ratio of 4:1, was used for the detection of rabbit IgG. Anti-hIL-6 antibody (AF-206-NA, R&D Systems, UK) labeled with Cy5 and having a dye-to-protein ratio of 5:1 was used for the detection of hIL-6. Analyte solution and tracer solution were each mixed in the ratio 1:1 and incubated for 1 h in the dark at 37° C.

3.5.2. Performance of Measurement

The pretreated, dry sensor chip with applied flow cell structure was placed in the measuring device. To perform an experiment, the dry sample vessel was rinsed with a continuous flow of measuring buffer (PBS, pH 7.4, 0.05% Tween 20, 0.1% BSA) at 0.25 ml/min for 5 min. To optimize the excitation conditions for luminescence excitation, the sensor chip with the sample cells located thereon and the solution located therein was adjusted for maximum in-coupling of the excitation light via the grating structure assigned to the respective measuring region, and the intensity of the light emitted from the measuring region was measured over a period of 1s. The preincubated standard solutions were added to the sample cell sequentially in ascending concentration from an autosampler (231XL, Gilson, USA) by means of a dispensing pump. On rinsing, residual solution was eliminated via the drainage system of the sample cell.

In the case of the detection of rabbit IgG, the total sample (1 ml) was applied under continuous flow (0.25 ml/min) for 4 min and during this period the binding of the analyte to the prepared sensor surface was measured in real time by means of the increase in fluorescence (measurement points every 30 s, FIG. 12). After then rinsing in each case for 8 min with buffer solution, the sample was applied in the next higher concentration. In the case of the detection of hIL-6, the sample was injected only briefly and rapidly (flow rate 1 ml/min), and the binding of the analyte molecules from the standing sample to the immobilized recognition elements thereof was then measured without flow for 30 min until a steady state was reached (measurement points every 60 s, FIG. 13a). In this case there was no rinsing step between sequential sample additions. The corrected signal curve, from the quotient of the measured fluorescence and reference signals, is shown in FIGS. 12 (rabbit IgG as analyte) and 13a (hIL-6 as analyte). The extent of nonspecific binding was determined in each case from the first measurement of a sample without analytes. The net binding signals for the different analyte concentrations were then determined as the difference between the corrected gross signal measured at the current analyte concentration and the nonspecific binding signal. From this, the signal concentration curves for rabbit IgG (FIG. 13b for hIL-6) were generated.

FIG. 13a shows the curve of the binding signals in a measurement series for detection of hIL-6. Throughout the experiment, which lasted more than 7 hours, no systematic decrease in signal height was observed, even after the saturation signals had been reached in the stationary state for the analyte concentration concerned. This means that no signal loss occurred either due to fading of the dye or to possible detachment of signal-emitting binding complexes from the surface, which indicates a very stable immobilization of the biological recognition elements used on the surface of the sensor platform. Vigorous rinsing (flow rate 2 ml/min for 5 min) of the sensor surface with relatively large quantities of sample, equivalent to the application of mechanical stress, also led to a stationary signal and not to a decrease in the signal, which is a further indication of the high degree of stability of the immobilization.

Performance hIL-6 Assay without Coupling Layer

To study the positive influence of a DDP monolayer on the intensity of the assay signals, i.e. the quantity of functionally immobilized recognition elements, and thus on the attainable limits of detection, the hIL-6 immunoassay on sensor chips was carried out for comparison purposes without an applied DDP monolayer, but with the surface otherwise pretreated in the same way. As shown in FIG. 13a, the binding signals did not attain more than 10% of the signals from experiments using precipitated adhesion-promoting layer of DDP. The lower signals are attributable to a lower surface occupancy and/or to denaturation of the indicator antibodies on the untreated surface.

EXAMPLE 4

Sandwich Immunoassays on Monolayers of Mixed Hydrophobically/Hydrophilically Terminated Alkyl Phosphates The aim of the experiment was to show that the assay signals and thus detection sensitivities of immunoassays can be substantially increased on sensor surfaces which are produced by precipitation of monolayers of defined mixtures of hydrophobically (alkyl) and hydrophilically (hydroxyl) terminated alkyl phosphates. As already shown, the contact angle of metal oxide surfaces with water can be selectively adjusted by appropriate mixing of hydrophilically and hydrophobically terminated alkyl phosphates. This permits a specific optimization of the number of functionally immobilized recognition elements, depending on the nature of the recognition element used. The antibodies described in Example 3 were used as recognition elements.

Sensor chip surfaces were prepared with monolayers of aqueous mixtures of DDP-OH:DDP in the ratio of 0:100, 20:80, 40:60, 60:40, 80:20 and 100:0 percent. The chips were further treated and the measurements conducted as described in Example 3. FIG. 14 shows the standardized signal responses for the mixtures used. In the case of the detection of rabbit IgG, the signal response for the optimum mixture may be increased by up to 300% over the value with a pure DDP layer. The optimum mixture ratio lies between 80:20 and 60:40 percent DDP-OH:DDP, thus with more of a hydrophilic surface. Similar values have been achieved in the assays for the detection of hIL-6.

EXAMPLE 5

Production of a Biocompatible Double Layer as Adhesion-Promoting Layer (comprising a DDP and a Lipid Layer) Free from Organic Solvent Residues As already shown, very hydrophobic monolayers on metal oxide surfaces can be produced by precipitation of DDP from aqueous phase. Such hydrophobic, self-assembled layers are highly suited to the precipitation of further monolayers, e.g. comprising natural or synthetic lipids. Double layers thus generated simulate on their surface the properties of natural cell membranes and are especially suitable for the functional immobilization of membrane-anchored or membrane-bound recognition elements such as cell receptors or even whole membrane particles, which are known to be very sensitive and to respond to contact with media having physicochemical properties other than those of the natural membrane environment by undergoing changes. Thus the smallest changes in protein structure resulting from contact with a hydrophobic, hard sensor surface can lead to a total failure of receptor function.

Part A) Production of Biocompatible Double Layers Comprising a Primary DDP Monolayer with a Hydrophobic Surface and a Secondary Lipid Monolayer which has Been Produced by Spontaneous Spreading of Lipid Vesicles on the Primary Hydrophobic Surface.

According to the description in Example 3, hydrophobic sensor surfaces were produced with a DPP monolayer. Lipid vesicles were produced from synthetic lipid 1-palmitoyl ($C_{16}$)-2-oleoyl ($C_{18}$)—SN-glycero-3-phosphocholine (POPC) (Avanti Polar Lipids, catalog no. 850457). To this end, 6 mg of dry POPC was taken up in 3 ml of vesicle buffer (150 mM NaCl, 10 mM phosphate buffer, 0.002% $NaN_3$, pH 7.5), incubated for about 12 h in the refrigerator at 4° C. and then mixed, which resulted in a turbid suspension. Monolayered lipid vesicles measuring about 100 nm were then produced by extrusion (about 20 times) through a 100 nm pore filter (extruder ?). Vesicle formation was observed on the basis of an increasing clarification of the suspension. The hydrophobic surfaces of the sensor chips were incubated with diluted vesicle suspension (0.5 mg/ml) for one hour at room temperature with sample vessels fitted. Surplus vesicle suspension is eliminated by thorough rinsing with vesicle buffer. The kinetics underlying the formation of a second monolayer of lipids by vesicle spreading was observed using fluorescently labeled vesicles comprising 0.1% of a lipid labeled with dye (1,2-dioleoyl($C_{18}$)—SN-glycero-3-phosphoethanolamine fluorescein (DOPE fluorescein) by means of fluorescence measurement in the measurement apparatus described in Example 3.4. The kinetics underlying the formation of the second lipid layer (with 0.1% lipid dye) on the DDP layer is shown in FIG. 15. The signal change between initial baseline and final signal level after rinsing of the surface corresponds to the signal of a monolayer. This signal amounts to about 50% of the signal upon the formation of a double layer of lipids fluorescently labeled in the same way when a similar vesicle suspension is incubated with a blank, hydrophilic metal oxide layer as sensor surface (without hydrophobic primary layer). Part B) Demonstration of the Biocompatibility of a DDP-Lipid Double Layer for the Immobilization of Membrane Receptors Detected by Means of a Binding Assay Using Native Membrane Fragments Immobilized on the Double Layer with Coupled Membrane Enzyme Na,K-Atpase.

In its function as an ion pump (of $K^+$ and $Na^+$ ions), the enzyme Na,K-ATPase—an integral component of physiological cell membranes—regulates the membrane potential of living cells. A fluorescence-based assay was developed for the specific binding of $K^+$ ions to the enzyme on sensor surfaces. The $K^+$ binding signal serves as a sensitive measure of enzyme function, i.e. the pumping of $K^+$ ions across the cell membrane. The ions required for the pumping process are provided by the specific binding of these ions to the protein.

Physiological membrane fragments which had coupled the membrane enzyme Na,K-ATPase to their membrane were immobilized on a double-layer system described in Part A, a DDP (from aqueous phase) and lipid layer on a planar waveguide chip as sensor platform. The functional and stable immobilization of membrane fragments and thus of the enzymes is demonstrated by the ability to generate $K^+$ binding signals described above. Upon otherwise comparable immobilization of membrane fragments on blank sensor chips without a double-layer system, the ability to generate the $K^+$ binding signal is lost. The biocompatible effect of the adhesion-promoting layer presented—in this case a double-layer system which is free of organic solvent residues and comprises a layer of alkyl phosphates and lipids respectively—on the functional immobilization of membrane proteins and whole membrane fragments is thus demonstrated. The immobilization of the membrane enzyme with the possibility of contact with the blank sensor surface leads to denaturation and thus loss of function of the protein to be studied.

Figure 1:
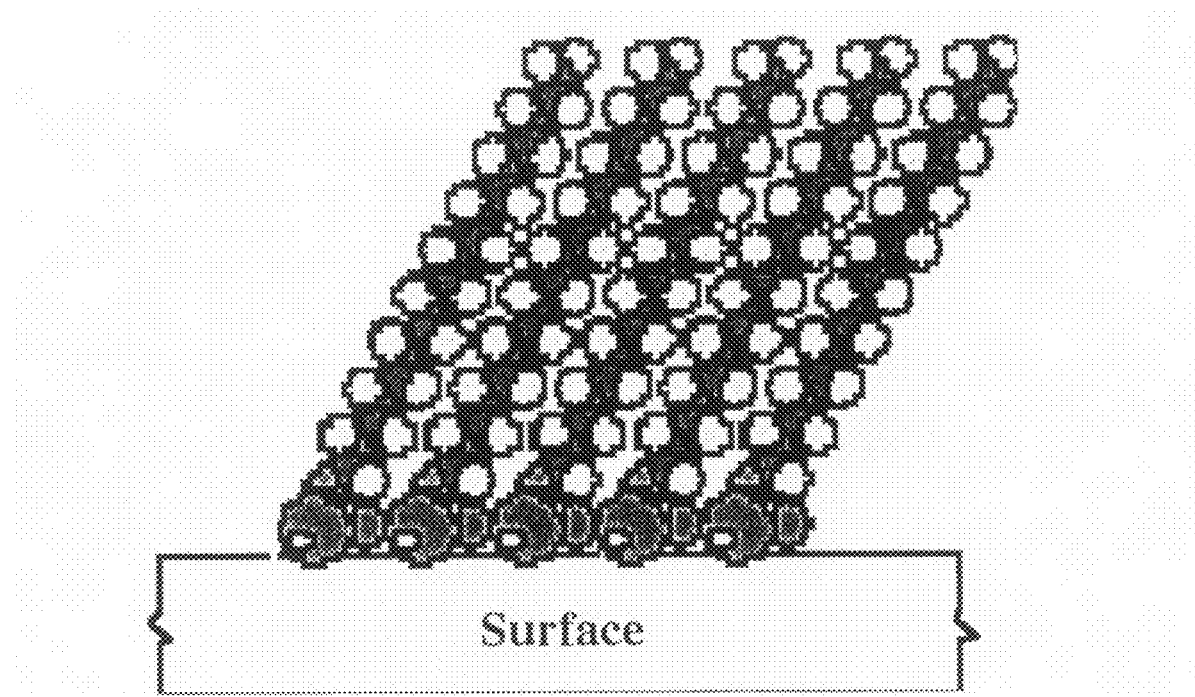
FIG. 1: Schematic representation of the ordered structure of alkyl phosphate SAMs on an oxide surface
Figure 2:
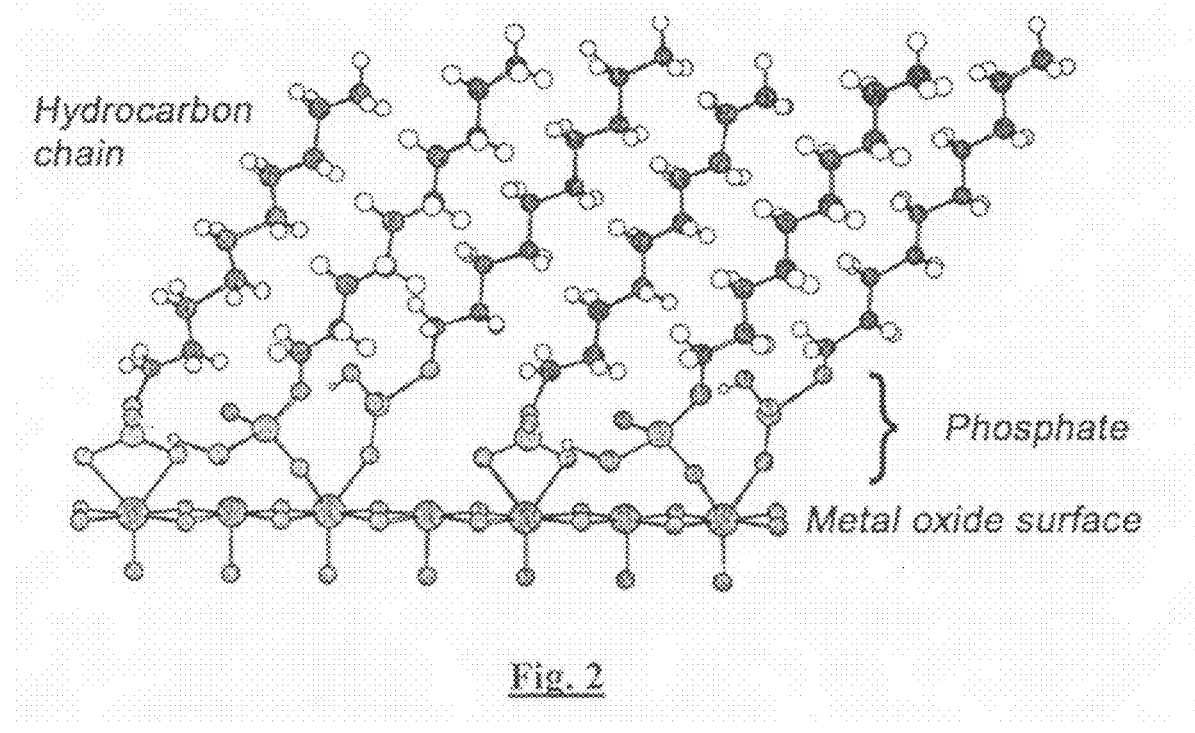
FIG. 2: Binding conditions in the assembled SAM layer between alkyl phosphates and a tantalum dioxide ($Ta_2O_5$) surface
Figure 3:
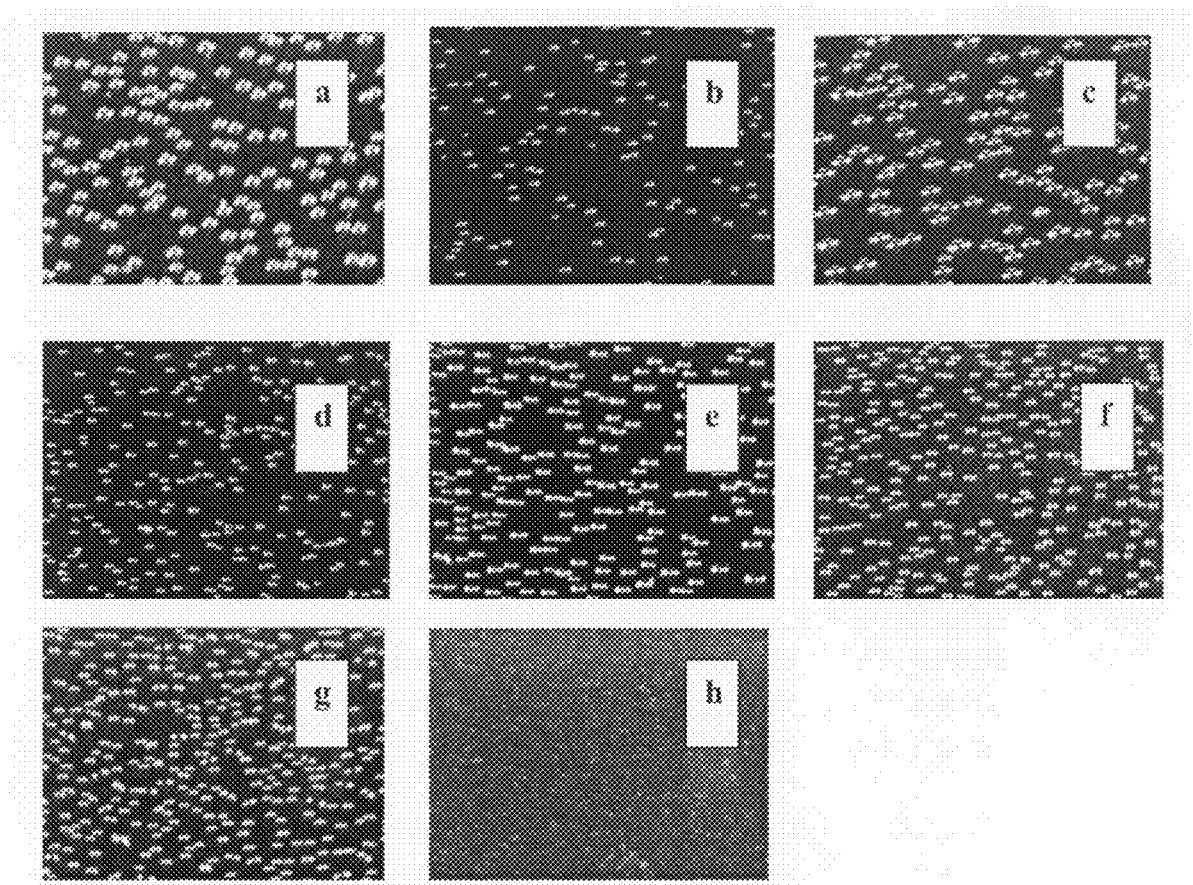
FIG. 3: Measurements of droplet density on $DDPO_4$ SAMs on different smooth metal oxide surfaces (image size: 1 $mm^2$): a) $Al_2O_3$, b) $Ta_2O_5$, c) $Nb_2O_5$, d) $ZrO_2$, e) $Fe_2O_3$, f) $TiO_2$, g) $Ti_{0.4}Si_{0.6}O_2$ and h) $SiO_2$. See text.
Figure 4:
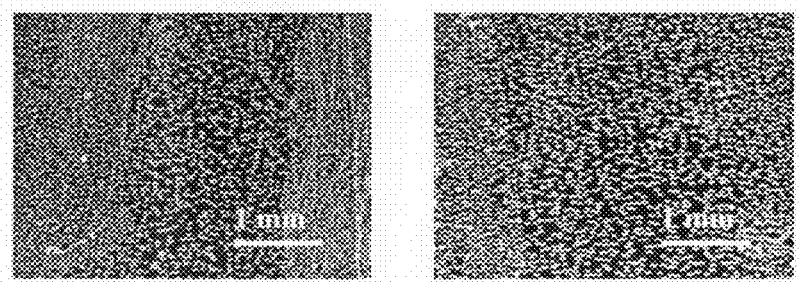
FIG. 4: $DDPO_4$ SAM on the $Ti_{0.4}Si_{0.6}O_2$ surface with a 2 mm wide strip of $Fe_2O_3$. The $Fe_2O_3$ surface is covered with $DDPO_4$ and is hydrophobic (low droplet density), whereas the substrate ($Ti_{0.4}Si_{0.6}O_2$) remains more hydrophilic, since it is not completely covered with $DDPO_4$.
Figure 5A:
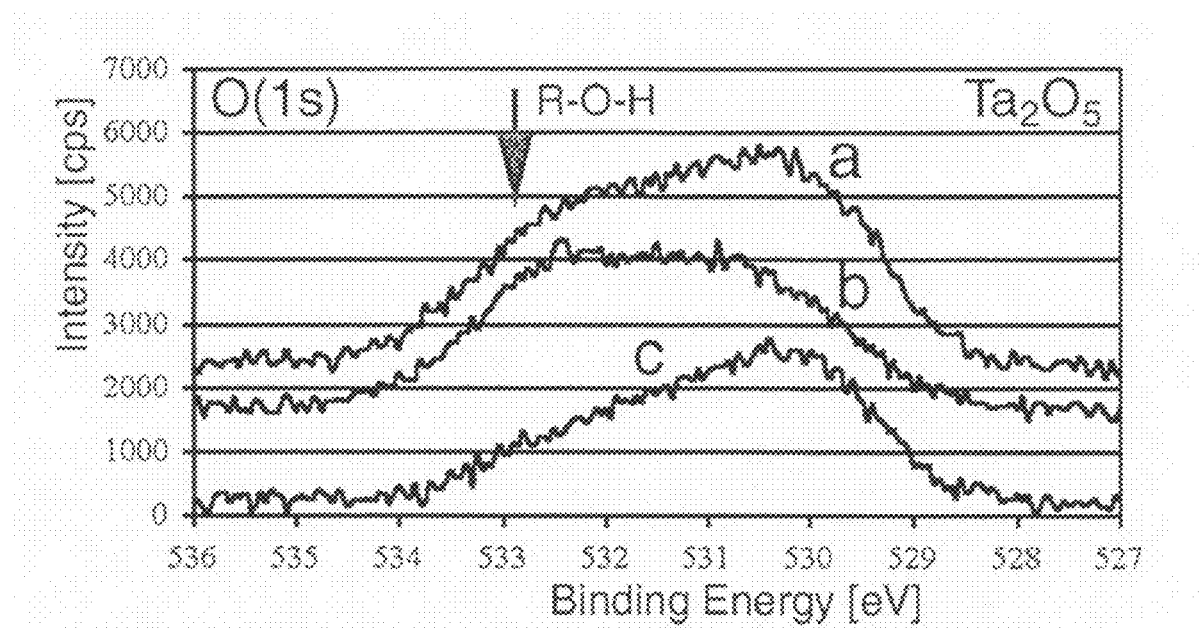
FIG. 5a: O1s XPS signal of OH-$DDPO_4$ SAMs on $Ta_2O_5$ substrates: The O1s spectra at the different exit angles (20.5°=top curve a; 11.5°=middle curve b) are compared with the corresponding signal of the $DDPO_4$ SAM (bottom curve c).
Figure 5B:
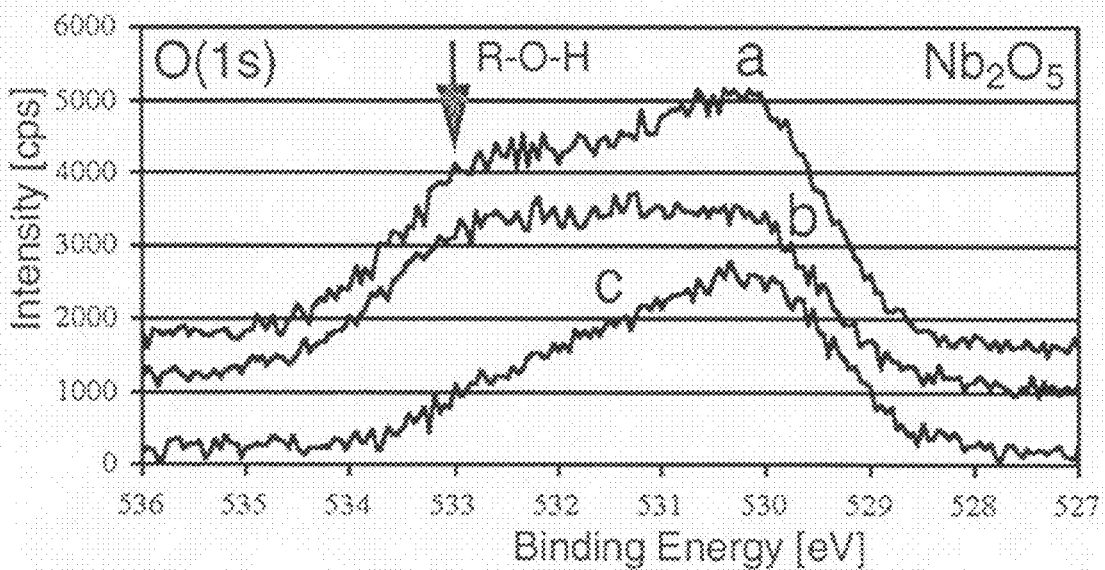
FIG. 5b: O1s XPS signal of OH-$DDPO_4$ SAMs on $Nb_2O_5$ substrates: The O1s spectra at the different exit angles (20.5°=top curve a; 11.5°=middle curve b) are compared with the corresponding signal of the $DDPO_4$ SAM (bottom curve c).
Figure 6A:
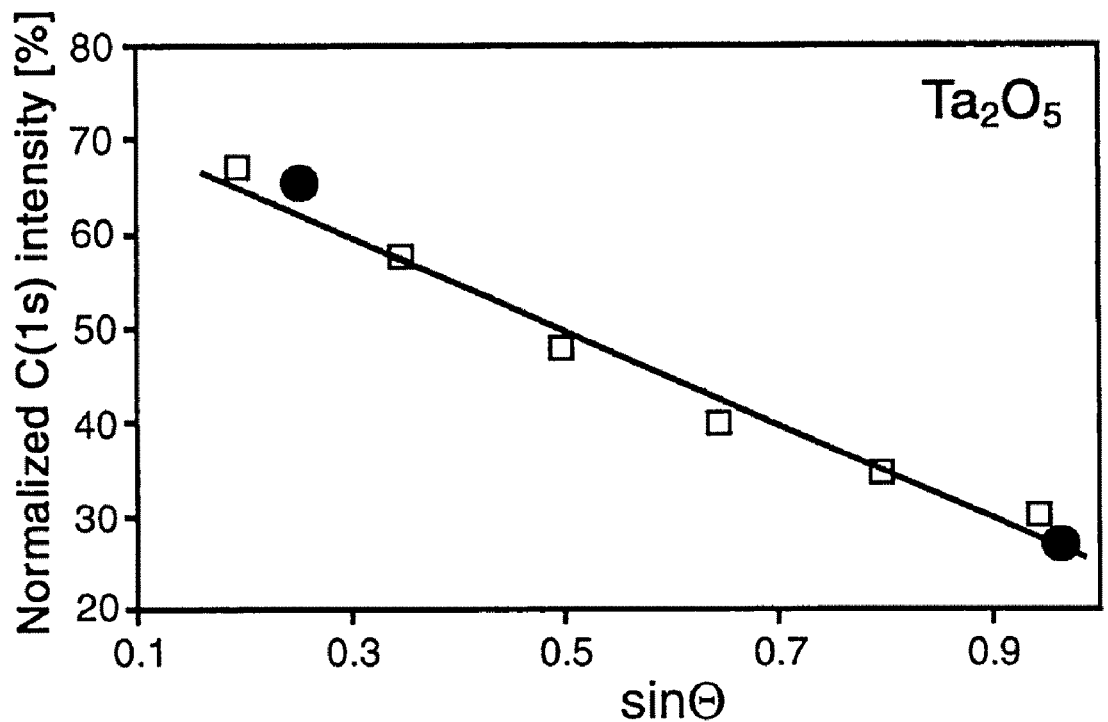
FIG. 6a: Comparison of the carbon concentration, determined by XPS, of OH-$DDPO_4$ and $DDPO_4$ SAMs on $Ta_2O_5$, as a function of the sine of detection angle $\Theta$. (OH-$DDPO_4$ carbon: solid circles; $DDPO_4$ carbon: open squares.)
Figure 6B:
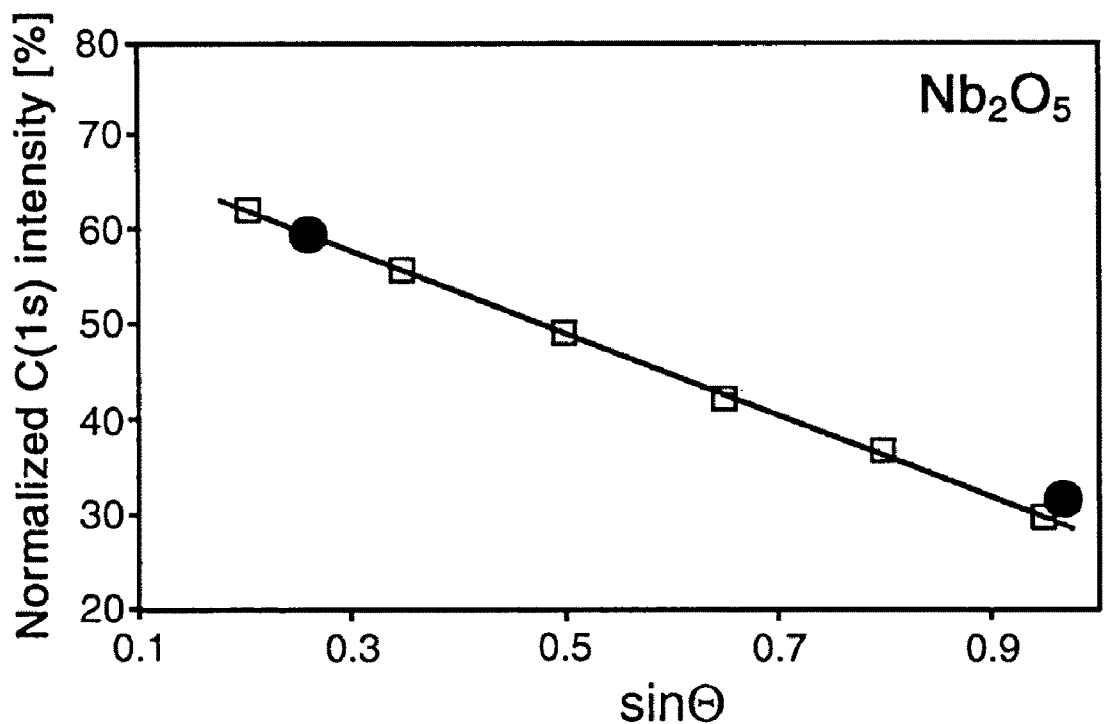
FIG. 6b: Comparison of the carbon concentration, determined by XPS, of OH-$DDPO_4$ and $DDPO_4$ SAMs on $Nb_2O_5$, as a function of the sine of detection angle $\Theta$). (OH-$DDPO_4$ carbon: solid circles; $DDPO_4$ carbon: open squares.)
Figure 7A:
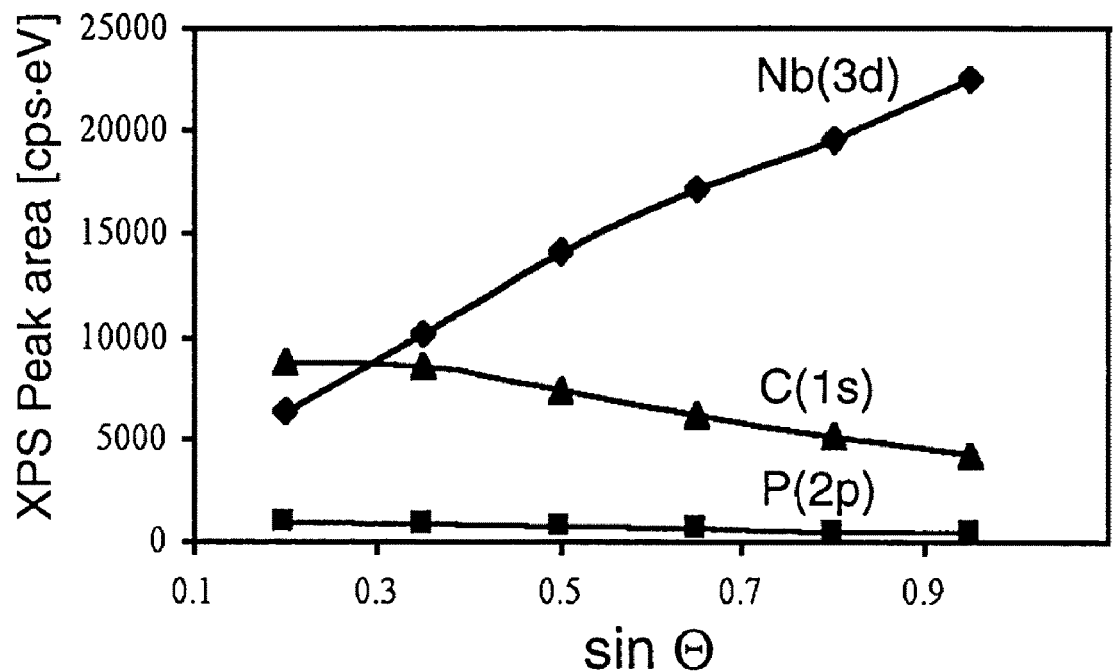
FIG. 7a: XPS peak areas as a function of the sine of detection angle $\Theta$ of Nb(3d), C(1s) and P(2p) on $Nb_2O_5$. The O(1s) signal was deconvoluted into three components: O($Nb_2O_5$): squares, O($PO_4$): triangles, O(ROH): circles. Similar results were also found in the case of the substrate $Ta_2O_5$.
Figure 7B:
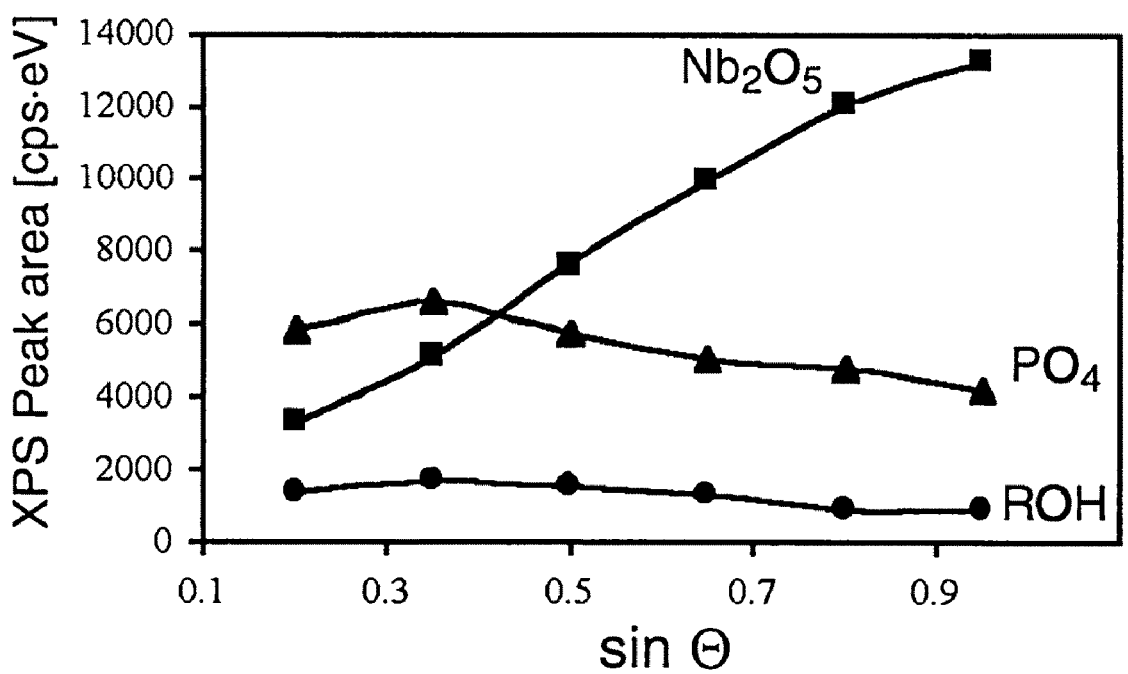
FIG. 7b: XPS peak areas as a function of the sine of detection angle $\Theta$ of the various oxygens for OH-$DDPO_4$ SAM on $Nb_2O_5$. The O(1s) signal was deconvoluted into three components: O($Nb_2O_5$): squares, O($PO_4$): triangles, O(ROH): circles. Similar results were also found in the case of the substrate $Ta_2O_5$.
Figure 8:
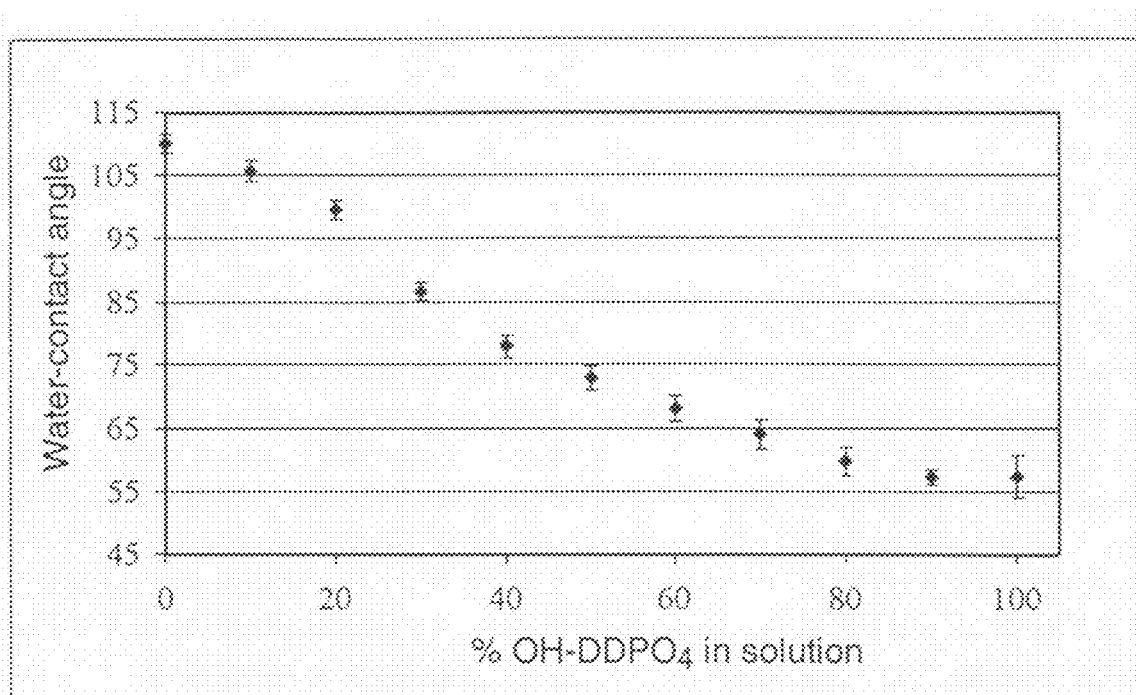
FIG. 8. Contact angle of mixed OH-$DDPO_4$/$DDPO_4$ SAMs on $Ta_2O_5$. The results are presented as a function of the mixture ratio in the SAM solution (vol-%). The total alkyl phosphate concentration was kept constant (0.5 mM).
Figure 9:
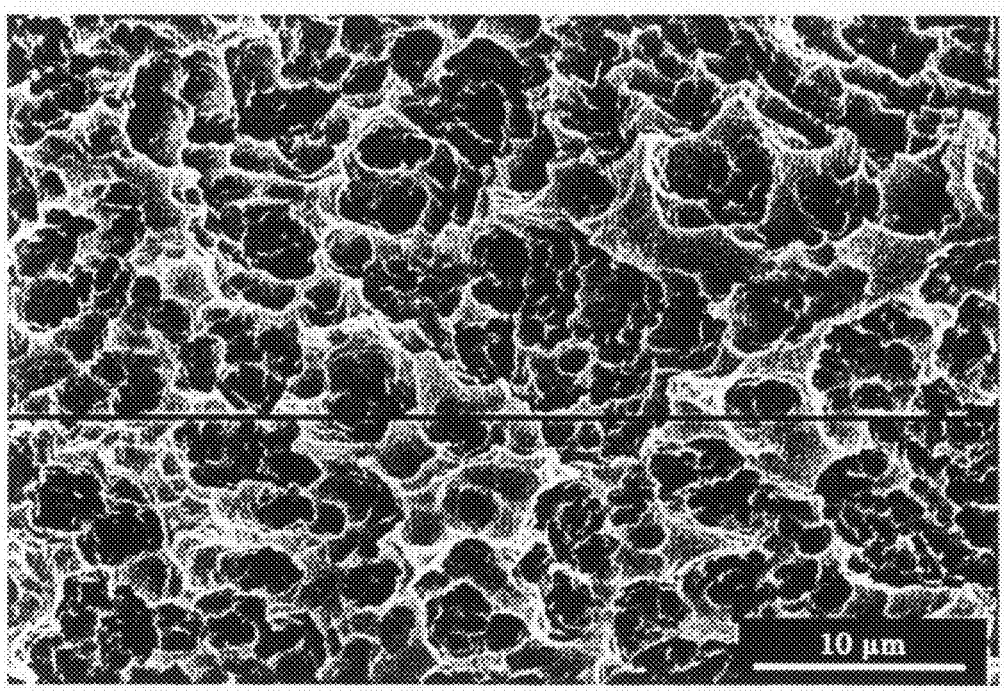
FIG. 9 Surface of a pure titanium (cp Ti) sample roughened by blasting and chemical etching. Origin of sample: Institut Straumann AG, Waldenburg, Switzerland. Scanning electron microscopy.
Figure 10:
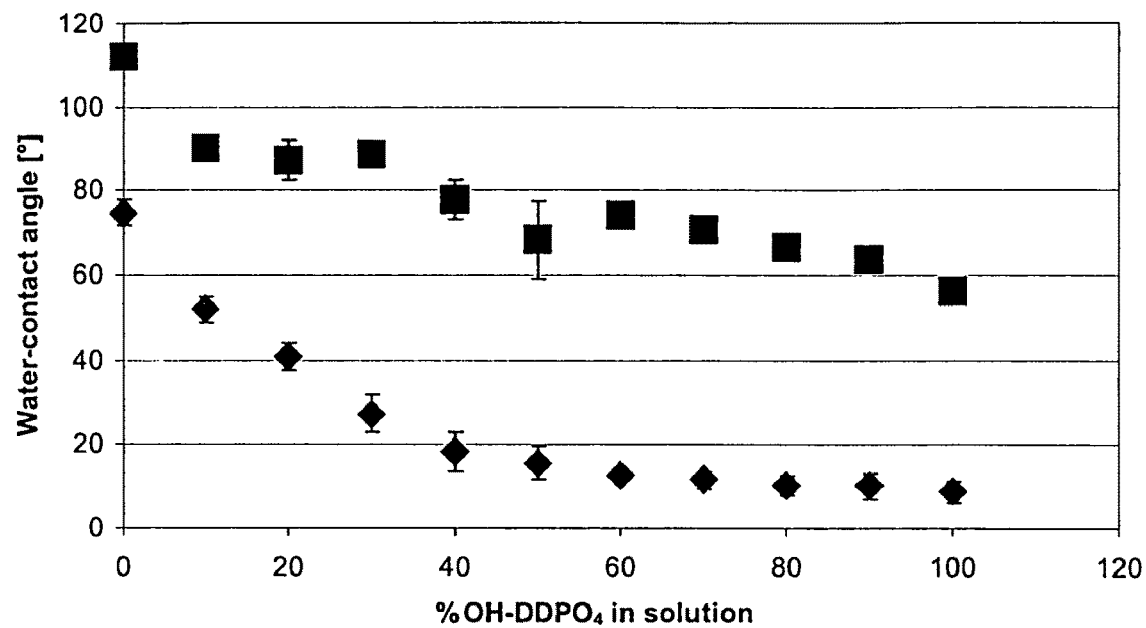
FIG. 10. Contact angle as a measure of the wettability of smooth, metallic titanium surfaces, treated with aqueous solutions of the salts $DDPO_4(NH_4)_2$, OH-$DDPO_4(NH_4)_2$ and mixtures thereof (upper data series: advancing contact angle, lower data series: receding contact angle).
Figure 11:
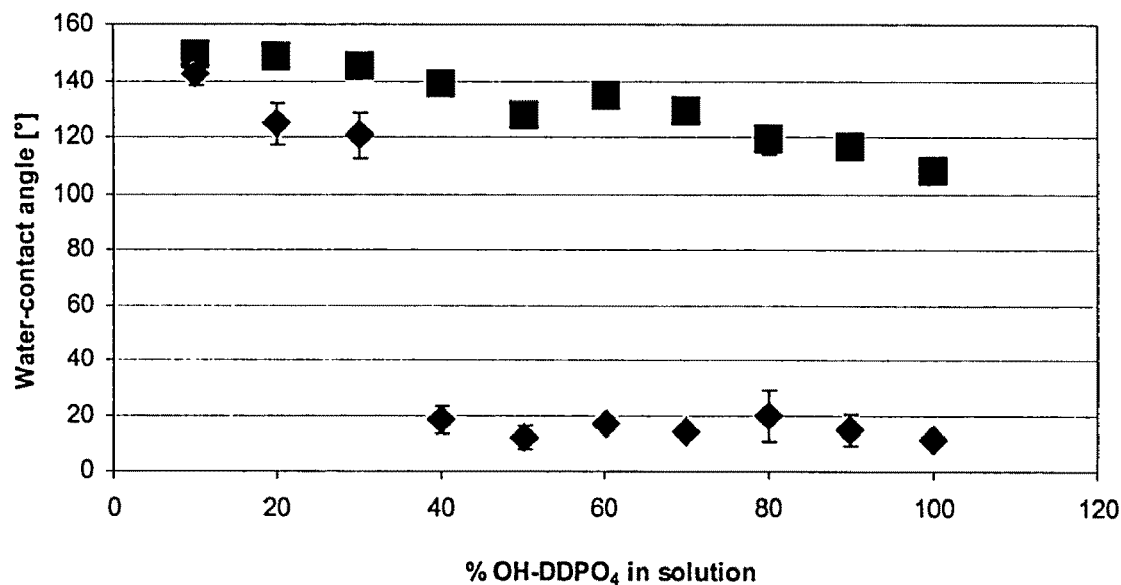
FIG. 11. Contact angle as a measure of the wettability of rough, metallic titanium surfaces, treated with aqueous solutions of the salts $DDPO_4(NH_4)_2$, OH-$DDPO_4(NH_4)_2$ and mixtures thereof (upper data series: advancing contact angle, lower data series: receding contact angle).
Figure 12:
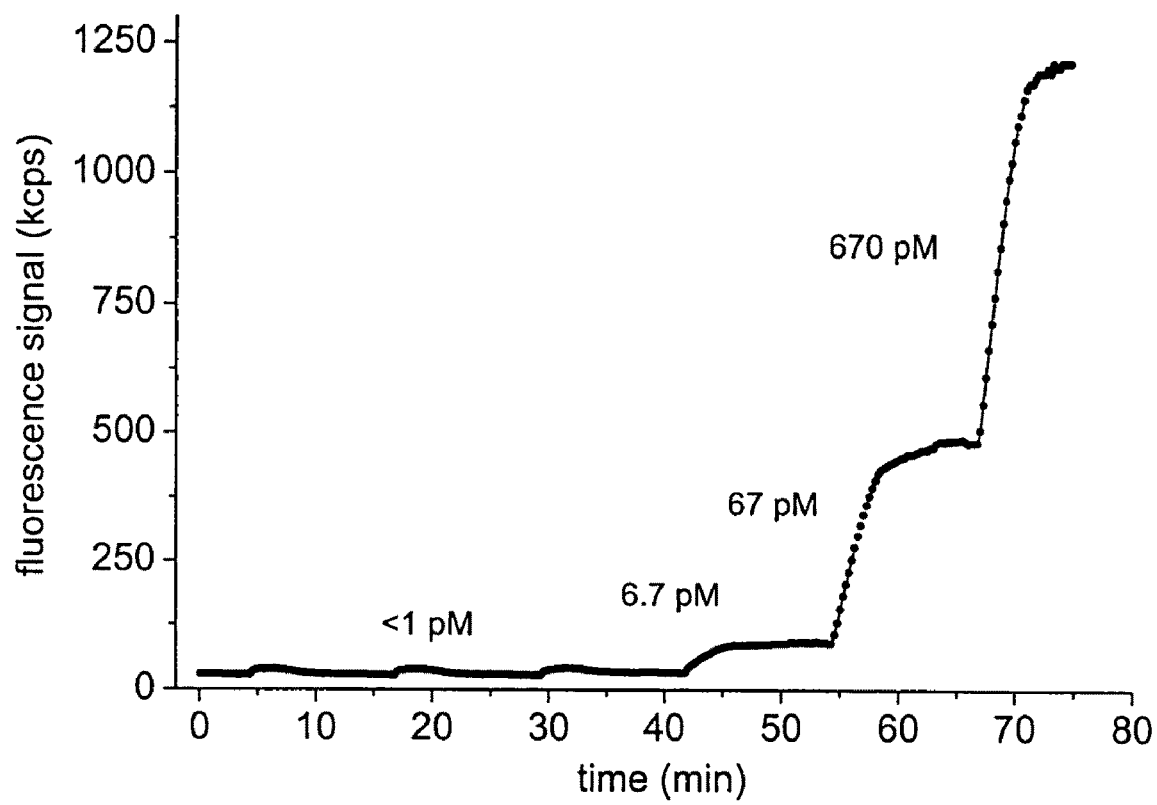
FIG. 12: Corrected signal curve upon the addition of increasing concentrations of the analyte rabbit IgG, detected by means of fluorescence-based sandwich assay on thin-layer waveguides as sensor platforms, on which the specific recognition antibodies have been immobilized on a monolayer of dodecylphosphate (DDP). In the sequential assay steps, the addition of the analyte over a period of 4 min is followed in each case by rinsing with buffer solution (8 min).
Figure 13A:
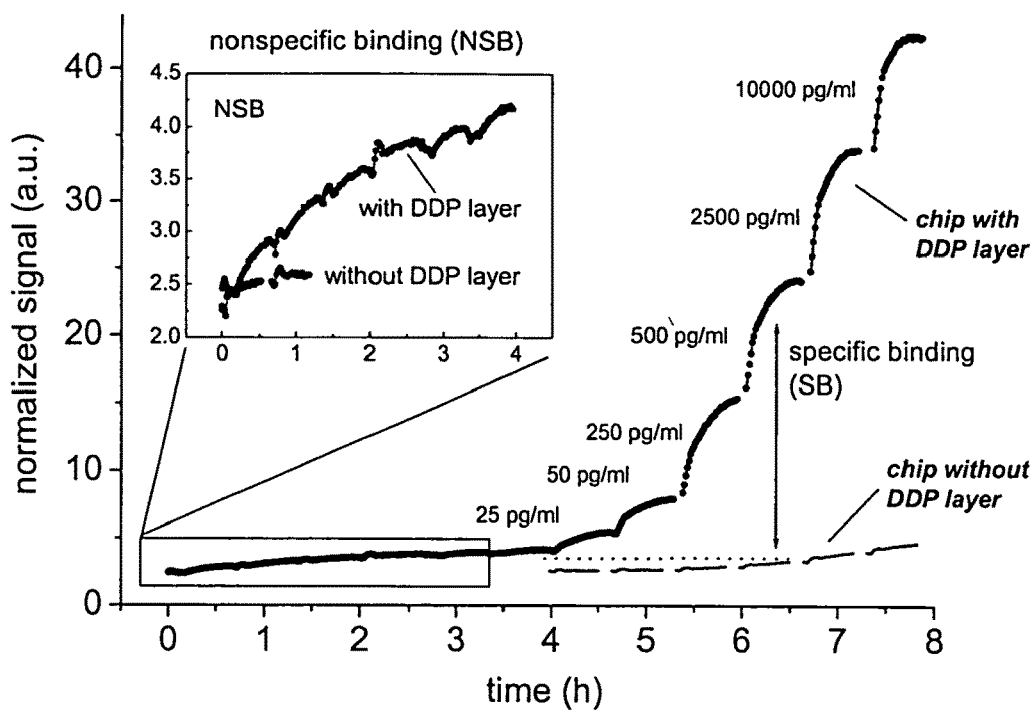
FIG. 13a: Corrected signal curve upon the addition of increasing concentrations of the analyte hIL-6, detected by means of fluorescence-based sandwich assay on thin-layer waveguides as sensor platforms, on which the specific recognition antibodies have been immobilized in the presence and the absence of a monolayer of dodecylphosphate (DDP). Clearly visible here are the marked signal increases in the presence of a DDP monolayer, indicating a functional immobilization of a large number of recognition antibodies.
Figure 13B:
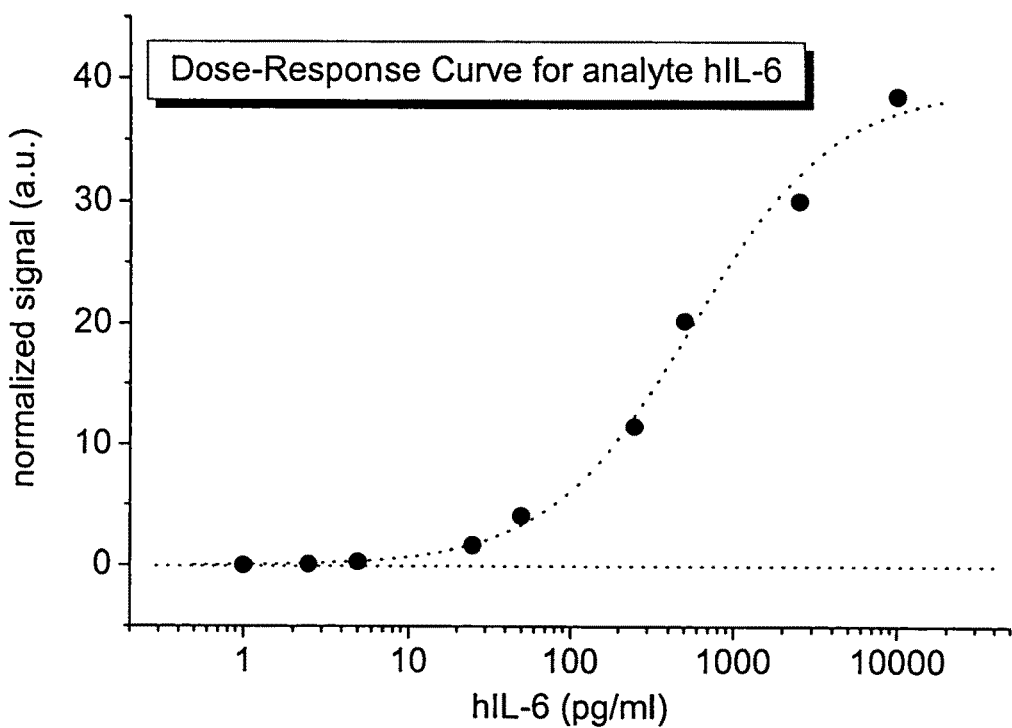
FIG. 13b: Signal-concentration function (dose-response curve) generated from the stationary signal responses according to FIG. 13a (chip with DDP monolayer). The course of the data points corresponds to a Langmuir binding isotherm (1:1 binding), which was fitted to the data.
Figure 14:
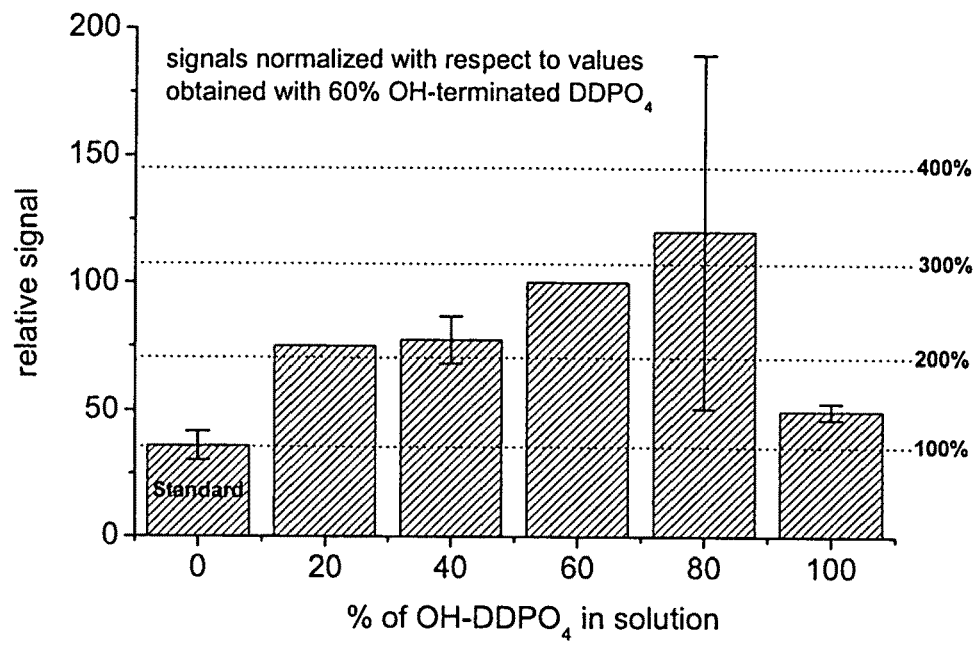
FIG. 14: Relative assay signals of experiments for the detection of rabbit IgG (250 µM), carried out on chip surfaces with monolayers precipitated from different, aqueous mixtures of OH-terminated DDP and hydrophobically terminated DDP. The error bars show the deviations of measurements on two chips. Values were standardized to the signals at 60% OH-terminated DDP portion.
Figure 15:
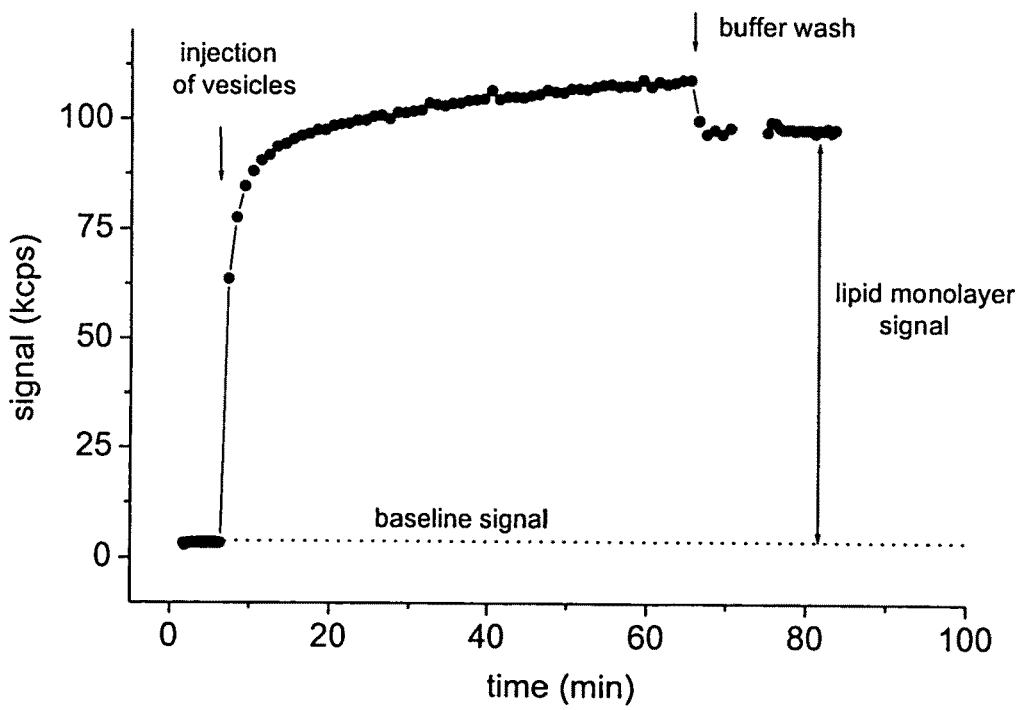
FIG. 15: Signal curve during the formation of a second monolayer of fluorescently labeled lipids (POPC with 0.1% DOPE fluorescein) by spreading of lipid vesicles (diameter about 110 nm) on a hydrophobic DDP monolayer on a metal oxide thin-layer waveguide as sensor platform.

The invention claimed is:
1. A method which comprises precipitating mono or multiple layers of organophosphoric acids of the general formula I (A)

Y—B—$OPO_3H_2$   (IA)

or of organophosphonic acids of the general formula I (B)

Y—B—$PO_3H_2$   (IB)

and the salts thereof, on a substrate surface of pure or mixed oxides, nitrides or carbides of metals or semiconductors, wherein B is an alkyl, alkenyl, alkinyl, aryl, aralkyl, hetaryl or hetarylalkyl residue and Y is hydrogen or a functional group from the hydroxy, carboxy, amino, optionally low-alkyl-substituted mono or dialkylamino series, thiol, or a negative acid group from the ester, phosphate, phosphonate, sulfate, sulfonate, maleimide, succinimydyl, epoxy, acrylate series, wherein a biological, biochemical or synthetic recognition element is coupled to B or Y by addition or substitution reaction, wherein compounds may also be added conferring on the substrate surface a resistance to protein adsorption and/or to cell adhesion and the B chain may optionally be comprised of one or more ethylene oxide groups, rather than one or more —CH2— groups, and wherein the organophosphoric acid or organophosphonic acid is precipitated from water-soluble salts of a compound of formula (IA) or (IB) for the treatment of these surfaces, of sensor platforms, implants and medical accessory devices, and wherein the biochemical, biological or synthetic recognition elements (coupled to B or Y) are selected from among the group of nucleic acids, such as DNA, RNA, oligonucleotides, nucleic acid analogs, such as PNA, monoclonal or polyclonal antibodies, peptides, enzymes, aptamers, synthetic peptide structures, soluble membrane-bound proteins and proteins isolated from a membrane, such as receptors, ligands thereof, antigens for antibodies, biotin, "histidine tag components" and complexing partners thereof.

2. A method which comprises precipitating mono or multiple layers of organophosphoric acids of the general formula I (A)

Y—B—OPO$_3$H$_2$   (IA)

or of organophosphonic acids of the general formula I (B)

Y—B—PO$_3$H$_2$   (IB)

and the salts thereof, on a substrate surface of pure or mixed oxides, nitrides or carbides of metals or semiconductors, wherein B is an alkyl, alkenyl, alkinyl, aryl, aralkyl, hetaryl or hetarylalkyl residue and Y is hydrogen or a functional group from the hydroxy, carboxy, amino, optionally low-alkyl-substituted mono or dialkylamino series, thiol, or a negative acid group from the ester, phosphate, phosphonate, sulfate, sulfonate, maleimide, succinimydyl, epoxy, acrylate series, wherein a biologically effective recognition element is coupled to B or Y by addition or substitution reaction, wherein compounds may also be added conferring on the substrate surface a resistance to protein adsorption and/or to cell adhesion and the B chain may optionally be comprised of one or more ethylene oxide groups, rather than one or more —CH2— groups, and wherein the organophosphoric acid or organophosphonic acid is precipitated from water-soluble salts of a compound of formula (IA) or (IB) for the treatment of these surfaces, of sensor platforms, implants and medical accessory devices, and wherein the biologically effective recognition element comprises peptides, proteins, glycoproteins, growth factor, such as TGF-β, or BMP (bone morphogenic protein).

3. A method which comprises precipitating mono or multiple layers of organophosphoric acids of the general formula I (A)

Y—B—OPO$_3$H$_2$   (IA)

or of organophosphonic acids of the general formula I (B)

Y—B—PO$_3$H$_2$   (IB)

and the salts thereof, on a substrate surface of pure or mixed oxides, nitrides or carbides of metals or semiconductors, wherein B is an alkyl, alkenyl, alkinyl, aryl, aralkyl, hetaryl or hetarylalkyl residue and Y is hydrogen or a functional group from the hydroxy, carboxy, amino, optionally low-alkyl-substituted mono or dialkylamino series, thiol, or a negative acid group from the ester, phosphate, phosphonate, sulfate, sulfonate, maleimide, succinimydyl, epoxy, acrylate series, wherein a biological, biochemical or synthetic indicator element may be coupled to B or Y by addition or substitution reaction, wherein compounds are also added conferring on the substrate surface a resistance to protein adsorption and/or to cell adhesion and the B chain may optionally be comprised of one or more ethylene oxide groups, rather than one or more —CH2— groups, and wherein the organophosphoric acid or organophosphonic acid is precipitated from water-soluble salts of a compound of formula (IA) or (IB) for the treatment of these surfaces, of sensor platforms, implants and medical accessory devices, and wherein the compounds which confer on the substrate surface a resistance to protein adsorption and/or to cell adhesion are selected from the group of compounds which are formed from oligo(ethylene oxide), phosphoryl choline, heparin, saccharides, albumins, especially bovine serum albumin or human serum albumin, casein, nonspecific, polyclonal or monoclonal, heterologous or for the analyte or analytes to be determined empirically nonspecific antibodies (especially for immunoassays), detergents (such as Tween 20), fragmented natural DNA or synthetic DNA not hybridizing with polynucleotides for analysis, such as a herring or salmon sperm extract (especially for polynucleotide hybridization assays), or also uncharged, but hydrophilic polymers, such as polyethylene glycols or dextrans.

4. A method which comprises precipitating mono or multiple layers of organophosphoric acids of the general formula I (A)

Y—B—OPO$_3$H$_2$   (IA)

or of organophosphonic acids of the general formula I (B)

Y—B—PO$_3$H$_2$   (IB)

and the salts thereof, on a substrate surface of pure or mixed oxides, nitrides or carbides of metals or semiconductors, wherein B is an alkyl, alkenyl, alkinyl, aryl, aralkyl, hetaryl or hetarylalkyl residue and Y is hydrogen or a functional group from the hydroxy, carboxy, amino, optionally low-alkyl-substituted mono or dialkylamino series, thiol, or a negative acid group from the ester, phosphate, phosphonate, sulfate, sulfonate, maleimide, succinimydyl, epoxy, acrylate series, wherein a biological, biochemical or synthetic recognition element is coupled to B or Y by addition or substitution reaction, wherein compounds are also added conferring on the substrate surface a resistance to protein adsorption and/or to cell adhesion in a SAM molecule and the B chain may optionally be comprised of one or more ethylene oxide groups, rather than one or more —CH2— groups, and wherein the organophosphoric acid or organophosphonic acid is precipitated from water-soluble salts of a compound of formula (IA) or (IB) for the treatment of these surfaces, of sensor platforms, implants and medical accessory devices.

5. A sensor platform having a surface of a mono or multiple layers of organophosphates and/or organophosphonates.

6. A sensor platform according to claim 5 comprising at least one array of biological or biochemical or synthetic recognition elements, immobilized in discrete measurement areas (d) for the specific recognition and/or binding of one or more analytes and/or specific interaction with said analytes.

7. A sensor platform according to claim 5 capable of detection of one or more analytes by means of labels selected from the group consisting of luminescence labels, especially luminescent intercalators or "molecular beacons", absorption labels, mass labels, especially metal colloids or plastic beads, spin labels, such as ESR or NMR labels, and radioactive labels.

8. A sensor platform according to claim 6 capable of detection of analyte based on the determination of a change in the effective refractive index as a result of molecular adsorption or desorption on the measurement areas (d).

9. A sensor platform according to claim 8 capable of detection of analyte based on determination of a change in conditions for generating a surface plasmon in a metal layer of a multiple layer system, wherein the metal layer preferably comprises gold or silver.

10. A sensor platform according to claim 6 capable of detection of analyte based on the determination of a change in one or more luminescences.

11. A sensor platform according to claim 10 capable of delivery of excitation light in a vertical illuminator.

12. A sensor platform according to claim 6, wherein material of the sensor platform that is in contact with the measurement areas is transparent or absorbent within a depth of at least 200 nm from the measurement areas in at least one excitation wavelength.

13. A sensor platform according to claim 11, wherein the delivery of the excitation light is in a transmission configuration.

14. A sensor platform according to claim 13, wherein material of the sensor platform is transparent in at least one excitation wavelength.

15. A sensor platform according to claim 5 formed as an optical waveguide which is preferably essentially planar.

16. A sensor platform according to claim 15 which comprises an optically transparent material selected from the group of silicates, e.g. glass or quartz, transparent thermoplastic or moldable plastic, for example polycarbonate, polyimide, acrylates, especially polymethylmethacrylate, and polystyrene.

17. A sensor platform according to claim 15 which comprises an optical thin-layer waveguide with a layer which is transparent in at least one excitation wavelength (a) on a layer which is likewise transparent in at least this excitation wavelength (b) with a lower refractive index than layer (a).

18. A method according to claim 1, wherein the mono or multiple layers of compounds of formula (IA) and/or (IB) are free of organic solvents.

19. A method according to claim 1, wherein the water-soluble salts of a compound of formula (IA) or (IB) are sodium, potassium and/or ammonium salts.

20. A method according to claim 1, wherein the pure or mixed oxides, nitrides or carbides of metals are solid bodies or layers on substrates of any kind and the metals are selected from the group consisting of tantalum, niobium, titanium, vanadium, zirconium, hafnium, molybdenum, tungsten, silicon and mixtures thereof.

21. A method according to claim 2, wherein the mono or multiple layers of compounds of formula (IA) and/or (IB) are free of organic solvents.

22. A method according to claim 2, wherein the water-soluble salts of a compound of formula (IA) or (IB) are sodium, potassium and/or ammonium salts.

23. A method according to claim 2, wherein the pure or mixed oxides, nitrides or carbides of metals are solid bodies or layers on substrates of any kind and the metals are selected from the group consisting of tantalum, niobium, titanium, vanadium, zirconium, hafnium, molybdenum, tungsten, silicon and mixtures thereof.

24. A method according to claim 3, wherein the mono or multiple layers of compounds of formula (IA) and/or (IB) are free of organic solvents.

25. A method according to claim 3, wherein the water-soluble salts of a compound of formula (IA) or (IB) are sodium, potassium and/or ammonium salts.

26. A method according to claim 3, wherein the pure or mixed oxides, nitrides or carbides of metals are solid bodies or layers on substrates of any kind and the metals are selected from the group consisting of tantalum, niobium, titanium, vanadium, zirconium, hafnium, molybdenum, tungsten, silicon and mixtures thereof.

27. A method according to claim 4, wherein the mono or multiple layers of compounds of formula (IA) and/or (IB) are free of organic solvents.

28. A method according to claim 4, wherein the water-soluble salts of a compound of formula (IA) or (IB) are sodium, potassium and/or ammonium salts.

29. A method according to claim 4, wherein the pure or mixed oxides, nitrides or carbides of metals are solid bodies or layers on substrates of any kind and the metals are selected from the group consisting of tantalum, niobium, titanium, vanadium, zirconium, hafnium, molybdenum, tungsten, silicon and mixtures thereof.

\* \* \* \* \*